United States Patent
Friedrich et al.

(10) Patent No.: US 12,082,899 B2
(45) Date of Patent: Sep. 10, 2024

(54) SURGICAL ROBOTICS SYSTEMS AND DEVICES HAVING A STERILE RESTART, AND METHODS THEREOF

(71) Applicant: Distalmotion SA, Epalinges (CH)

(72) Inventors: Michael Friedrich, Bern (CH); Romain Michel Miran Farkas, Lausanne (CH); Philippe Allemann, Vevey (CH); Didier Christian Geffrotin, Lausanne (CH); Nicolas Paul Marcel Boch, Lausanne (CH); Christopher Emmanuel Lieberherr, Morges (CH); Laurent Renaud Uldry, Prilly (CH); Werner Pirkl, Penthéréaz (CH)

(73) Assignee: Distalmotion SA, Epalinges (CH)

( * ) Notice: Subject to any disclaimer, the term of this patent is extended or adjusted under 35 U.S.C. 154(b) by 0 days.

(21) Appl. No.: 18/504,067

(22) Filed: Nov. 7, 2023

(65) Prior Publication Data
US 2024/0268909 A1    Aug. 15, 2024

Related U.S. Application Data

(63) Continuation of application No. 18/167,779, filed on Feb. 10, 2023, now Pat. No. 11,844,585.

(51) Int. Cl.
*A61B 34/37* (2016.01)
*A61B 34/00* (2016.01)

(52) U.S. Cl.
CPC .............. *A61B 34/37* (2016.02); *A61B 34/74* (2016.02)

(58) Field of Classification Search
CPC .......... A61B 34/37; A61B 34/74; A61B 34/30

USPC ................. 700/245–264; 318/568.11–568.25
See application file for complete search history.

(56) References Cited

U.S. PATENT DOCUMENTS

| | | | |
|---|---|---|---|
| 2,764,301 | A | 9/1956 | Goertz et al. |
| 2,771,199 | A | 11/1956 | Jelatis |
| 2,774,488 | A | 12/1956 | Goertz et al. |
| 2,846,084 | A | 8/1958 | Goertz et al. |
| 3,065,863 | A | 11/1962 | Saunders, Jr. |

(Continued)

FOREIGN PATENT DOCUMENTS

| | | |
|---|---|---|
| CN | 101027010 A | 8/2007 |
| CN | 101584594 A | 11/2009 |

(Continued)

OTHER PUBLICATIONS

US 9,232,978 B2, 01/2016, Shellenberger (withdrawn)

(Continued)

*Primary Examiner* — Jaime Figueroa
(74) *Attorney, Agent, or Firm* — Cooley LLP

(57) ABSTRACT

The present disclosure relates to surgical robotic systems having a master console and slave manipulators, with components and features for enabling a restart without compromising the sterility of the surgical robotic system. In some embodiments, an apparatus can include a restart of a surgical robotic system that is configured to be activated by a sterile user from within a sterile field without compromising the sterile field, and a controller operatively coupled to the restart that is configured to detect that the restart has been activated and, in response to detecting that the restart has been activated, restart the surgical robotic system.

23 Claims, 12 Drawing Sheets

(56) References Cited

U.S. PATENT DOCUMENTS

| | | | |
|---|---|---|---|
| 3,095,096 A | 6/1963 | Chesley | |
| 3,212,651 A | 10/1965 | Specht et al. | |
| 3,261,480 A | 7/1966 | Haaker et al. | |
| 3,297,172 A | 1/1967 | Haaker et al. | |
| 3,391,801 A | 7/1968 | Haaker | |
| 3,425,569 A | 2/1969 | Haaker | |
| 4,221,516 A | 9/1980 | Haaker et al. | |
| 4,522,196 A | 6/1985 | Cunningham et al. | |
| 4,756,655 A | 7/1988 | Jameson | |
| 5,147,357 A | 9/1992 | Rose et al. | |
| 5,176,352 A | 1/1993 | Braun | |
| 5,207,114 A | 5/1993 | Salisbury, Jr. et al. | |
| 5,209,747 A | 5/1993 | Knoepfler | |
| 5,304,203 A | 4/1994 | El-Mallawany et al. | |
| 5,308,358 A | 5/1994 | Bond et al. | |
| 5,330,502 A | 7/1994 | Hassler et al. | |
| 5,368,606 A | 11/1994 | Marlow et al. | |
| 5,383,888 A | 1/1995 | Zvenyatsky et al. | |
| 5,484,435 A | 1/1996 | Fleenor et al. | |
| 5,591,119 A | 1/1997 | Adair | |
| 5,599,151 A | 2/1997 | Daum et al. | |
| 5,603,723 A | 2/1997 | Aranyi et al. | |
| 5,631,973 A | 5/1997 | Green | |
| 5,649,955 A | 7/1997 | Hashimoto et al. | |
| 5,649,956 A | 7/1997 | Jensen et al. | |
| 5,709,219 A * | 1/1998 | Chen | A63F 13/285 |
| | | | 600/595 |
| 5,710,870 A * | 1/1998 | Ohm | B25J 19/02 |
| | | | 700/262 |
| 5,716,352 A | 2/1998 | Viola et al. | |
| 5,735,874 A | 4/1998 | Measamer et al. | |
| 5,779,727 A | 7/1998 | Orejola | |
| 5,784,542 A | 7/1998 | Ohm et al. | |
| 5,792,045 A | 8/1998 | Adair | |
| 5,797,900 A | 8/1998 | Madhani et al. | |
| 5,810,716 A | 9/1998 | Mukherjee et al. | |
| 5,810,805 A | 9/1998 | Sutcu et al. | |
| 5,828,813 A | 10/1998 | Ohm | |
| 5,908,436 A | 6/1999 | Cuschieri et al. | |
| 5,931,832 A | 8/1999 | Jensen | |
| 5,951,587 A | 9/1999 | Qureshi et al. | |
| 5,976,122 A | 11/1999 | Madhani et al. | |
| 6,026,701 A | 2/2000 | Reboulet | |
| 6,063,095 A | 5/2000 | Wang et al. | |
| 6,132,368 A | 10/2000 | Cooper | |
| 6,197,017 B1 | 3/2001 | Brock et al. | |
| 6,206,903 B1 | 3/2001 | Ramans | |
| 6,233,504 B1 | 5/2001 | Das et al. | |
| 6,281,651 B1 | 8/2001 | Haanpaa et al. | |
| 6,312,435 B1 | 11/2001 | Wallace et al. | |
| 6,331,181 B1 | 12/2001 | Tierney et al. | |
| 6,358,249 B1 | 3/2002 | Chen et al. | |
| 6,361,534 B1 | 3/2002 | Chen et al. | |
| 6,364,879 B1 | 4/2002 | Chen et al. | |
| 6,371,952 B1 | 4/2002 | Madhani et al. | |
| 6,375,610 B2 | 4/2002 | Verschuur | |
| 6,385,509 B2 | 5/2002 | Das et al. | |
| 6,394,998 B1 | 5/2002 | Wallace et al. | |
| 6,435,794 B1 | 8/2002 | Springer | |
| 6,436,107 B1 | 8/2002 | Wang et al. | |
| 6,459,926 B1 | 10/2002 | Nowlin et al. | |
| 6,491,701 B2 | 12/2002 | Tierney et al. | |
| 6,504,456 B2 | 1/2003 | Iio et al. | |
| 6,554,844 B2 | 4/2003 | Lee et al. | |
| 6,587,750 B2 | 7/2003 | Gerbi et al. | |
| 6,594,552 B1 | 7/2003 | Nowlin et al. | |
| 6,659,939 B2 * | 12/2003 | Moll | A61B 34/35 |
| | | | 600/102 |
| 6,671,581 B2 | 12/2003 | Niemeyer et al. | |
| 6,699,177 B1 | 3/2004 | Wang et al. | |
| 6,786,896 B1 | 9/2004 | Madhani et al. | |
| 6,788,999 B2 | 9/2004 | Green | |
| 6,799,065 B1 | 9/2004 | Niemeyer | |
| 6,840,938 B1 | 1/2005 | Morley et al. | |
| 6,850,817 B1 | 2/2005 | Green | |
| 6,852,107 B2 | 2/2005 | Wang et al. | |
| 6,879,880 B2 | 4/2005 | Nowlin et al. | |
| 6,902,560 B1 | 6/2005 | Morley et al. | |
| 6,913,613 B2 | 7/2005 | Schwarz et al. | |
| 6,951,535 B2 | 10/2005 | Ghodoussi et al. | |
| 6,991,627 B2 | 1/2006 | Madhani et al. | |
| 6,994,708 B2 | 2/2006 | Manzo | |
| 7,025,064 B2 | 4/2006 | Wang et al. | |
| 7,048,745 B2 | 5/2006 | Tierney et al. | |
| 7,083,571 B2 | 8/2006 | Wang et al. | |
| 7,090,637 B2 | 8/2006 | Danitz et al. | |
| 7,101,363 B2 | 9/2006 | Nishizawa et al. | |
| 7,122,032 B2 | 10/2006 | Shinmura et al. | |
| 7,204,836 B2 | 4/2007 | Wagner et al. | |
| 7,206,627 B2 * | 4/2007 | Abovitz | A61B 34/74 |
| | | | 600/407 |
| 7,214,230 B2 * | 5/2007 | Brock | A61B 34/30 |
| | | | 606/139 |
| 7,232,440 B2 | 6/2007 | Dumbauld et al. | |
| 7,241,289 B2 | 7/2007 | Braun | |
| 7,306,597 B2 | 12/2007 | Manzo | |
| 7,316,681 B2 | 1/2008 | Madhani et al. | |
| 7,338,513 B2 | 3/2008 | Lee et al. | |
| 7,364,582 B2 | 4/2008 | Lee | |
| 7,373,219 B2 | 5/2008 | Nowlin et al. | |
| 7,398,707 B2 | 7/2008 | Morley et al. | |
| 7,481,824 B2 | 1/2009 | Boudreaux et al. | |
| 7,549,998 B2 | 6/2009 | Braun | |
| 7,594,912 B2 | 9/2009 | Cooper et al. | |
| 7,604,642 B2 * | 10/2009 | Brock | A61B 17/00234 |
| | | | 606/1 |
| 7,608,039 B1 | 10/2009 | Todd | |
| 7,615,002 B2 | 11/2009 | Rothweiler et al. | |
| 7,615,067 B2 | 11/2009 | Lee et al. | |
| 7,674,255 B2 | 3/2010 | Braun | |
| 7,695,481 B2 | 4/2010 | Wang et al. | |
| 7,699,855 B2 | 4/2010 | Anderson et al. | |
| 7,713,190 B2 * | 5/2010 | Brock | A61B 90/36 |
| | | | 600/114 |
| 7,756,036 B2 | 7/2010 | Druke et al. | |
| 7,819,894 B2 | 10/2010 | Mitsuishi et al. | |
| 7,824,401 B2 | 11/2010 | Manzo et al. | |
| 7,828,798 B2 | 11/2010 | Buysse et al. | |
| 7,833,156 B2 | 11/2010 | Williams et al. | |
| 7,890,211 B2 | 2/2011 | Green | |
| 7,914,521 B2 | 3/2011 | Wang et al. | |
| 7,976,458 B2 | 7/2011 | Stefanchik et al. | |
| 8,048,084 B2 | 11/2011 | Schneid | |
| 8,105,320 B2 | 1/2012 | Manzo | |
| 8,114,017 B2 | 2/2012 | Bacher | |
| 8,137,263 B2 | 3/2012 | Marescaux et al. | |
| 8,142,447 B2 | 3/2012 | Cooper et al. | |
| 8,224,485 B2 | 7/2012 | Unsworth | |
| 8,246,617 B2 | 8/2012 | Welt et al. | |
| 8,267,958 B2 | 9/2012 | Braun | |
| 8,287,469 B2 | 10/2012 | Stefanchik et al. | |
| 8,292,889 B2 | 10/2012 | Cunningham et al. | |
| 8,306,656 B1 | 11/2012 | Schaible et al. | |
| 8,308,738 B2 | 11/2012 | Nobis et al. | |
| 8,332,072 B1 | 12/2012 | Schaible et al. | |
| 8,336,751 B2 | 12/2012 | Scirica | |
| 8,353,898 B2 | 1/2013 | Lutze et al. | |
| 8,357,161 B2 | 1/2013 | Mueller | |
| 8,382,742 B2 | 2/2013 | Hermann et al. | |
| 8,388,516 B2 | 3/2013 | Sholev | |
| 8,403,832 B2 | 3/2013 | Cunningham et al. | |
| 8,414,475 B2 | 4/2013 | Sholev | |
| 8,418,904 B2 | 4/2013 | Wenchell et al. | |
| 8,423,186 B2 | 4/2013 | Itkowitz et al. | |
| 8,433,389 B2 | 4/2013 | Geiger et al. | |
| 8,435,171 B2 | 5/2013 | Sholev | |
| 8,437,754 B2 | 5/2013 | Kubota et al. | |
| 8,444,631 B2 * | 5/2013 | Yeung | A61B 34/30 |
| | | | 606/1 |
| 8,496,152 B2 | 7/2013 | Viola | |
| 8,518,024 B2 | 8/2013 | Williams et al. | |
| 8,523,900 B2 | 9/2013 | Jinno et al. | |
| 8,540,748 B2 | 9/2013 | Murphy et al. | |
| 8,560,118 B2 | 10/2013 | Greer et al. | |

(56) References Cited

U.S. PATENT DOCUMENTS

| | | |
|---|---|---|
| 8,562,592 B2 | 10/2013 | Conlon et al. |
| 8,568,444 B2 | 10/2013 | Cunningham |
| 8,579,176 B2 | 11/2013 | Smith et al. |
| 8,591,397 B2 | 11/2013 | Berkelman et al. |
| 8,597,280 B2 | 12/2013 | Cooper et al. |
| 8,602,287 B2 | 12/2013 | Yates et al. |
| 8,603,077 B2 | 12/2013 | Cooper et al. |
| 8,616,431 B2 | 12/2013 | Timm et al. |
| 8,617,203 B2 | 12/2013 | Stefanchik et al. |
| 8,620,473 B2 | 12/2013 | Diolaiti et al. |
| 8,663,270 B2 | 3/2014 | Donnigan et al. |
| 8,668,689 B2 | 3/2014 | Dumbauld et al. |
| 8,668,702 B2 | 3/2014 | Awtar et al. |
| 8,690,755 B2 | 4/2014 | Sholev |
| 8,696,666 B2 | 4/2014 | Sanai et al. |
| 8,709,000 B2 | 4/2014 | Madhani et al. |
| 8,738,181 B2 | 5/2014 | Greer et al. |
| 8,746,252 B2 | 6/2014 | McGrogan et al. |
| 8,761,930 B2 | 6/2014 | Nixon |
| 8,763,879 B2 * | 7/2014 | Shelton, IV ............ A61B 34/76 227/19 |
| 8,768,509 B2 | 7/2014 | Unsworth |
| 8,792,688 B2 | 7/2014 | Unsworth |
| 8,801,752 B2 | 8/2014 | Fortier et al. |
| 8,816,628 B2 | 8/2014 | Nowlin et al. |
| 8,818,560 B2 | 8/2014 | Kishi |
| 8,821,480 B2 | 9/2014 | Burbank |
| 8,827,135 B2 | 9/2014 | Amid et al. |
| 8,828,046 B2 | 9/2014 | Stefanchik et al. |
| 8,845,517 B2 | 9/2014 | Russo |
| 8,845,622 B2 | 9/2014 | Paik et al. |
| 8,870,049 B2 | 10/2014 | Amid et al. |
| 8,870,867 B2 | 10/2014 | Walberg et al. |
| 8,887,979 B2 | 11/2014 | Mastri et al. |
| 8,894,674 B2 | 11/2014 | Balanev et al. |
| 8,919,348 B2 | 12/2014 | Williams et al. |
| 8,930,027 B2 | 1/2015 | Schaible et al. |
| 8,945,098 B2 | 2/2015 | Seibold et al. |
| 8,961,499 B2 | 2/2015 | Paik et al. |
| 8,961,514 B2 | 2/2015 | Garrison |
| 8,968,187 B2 | 3/2015 | Kleyman et al. |
| 8,989,844 B2 | 3/2015 | Cinquin et al. |
| 8,992,564 B2 | 3/2015 | Jaspers |
| 9,023,015 B2 | 5/2015 | Penna |
| 9,033,998 B1 | 5/2015 | Schaible et al. |
| 9,044,238 B2 | 6/2015 | Orszulak |
| 9,052,710 B1 | 6/2015 | Farwell |
| 9,084,606 B2 | 7/2015 | Greep |
| 9,113,860 B2 | 8/2015 | Viola et al. |
| 9,113,861 B2 | 8/2015 | Martin et al. |
| 9,131,986 B2 | 9/2015 | Greer et al. |
| 9,149,339 B2 | 10/2015 | Unsworth |
| 9,192,459 B2 * | 11/2015 | Bonutti ............... A61G 13/0054 |
| 9,204,939 B2 | 12/2015 | Frimer et al. |
| 9,216,013 B2 | 12/2015 | Scirica et al. |
| 9,244,523 B2 | 1/2016 | Ogawa et al. |
| 9,295,379 B2 | 3/2016 | Sholev |
| 9,307,894 B2 | 4/2016 | Von Grünberg et al. |
| 9,333,040 B2 | 5/2016 | Shellenberger et al. |
| 9,345,545 B2 | 5/2016 | Shellenberger et al. |
| 9,360,934 B2 | 6/2016 | Ruiz Morales et al. |
| 9,421,003 B2 | 8/2016 | Williams et al. |
| 9,474,580 B2 | 10/2016 | Hannaford et al. |
| 9,480,531 B2 | 11/2016 | Von Grünberg |
| 9,492,240 B2 | 11/2016 | Itkowitz et al. |
| 9,603,672 B2 | 3/2017 | Shellenberger et al. |
| 9,669,542 B2 | 6/2017 | Karguth et al. |
| 9,696,700 B2 | 7/2017 | Beira et al. |
| 9,730,717 B2 | 8/2017 | Katsuki et al. |
| 9,757,204 B2 | 9/2017 | Frimer et al. |
| 9,757,206 B2 | 9/2017 | Frimer et al. |
| 9,763,741 B2 | 9/2017 | Alvarez et al. |
| 9,782,229 B2 * | 10/2017 | Crawford ............ A61B 17/8866 |
| 9,795,282 B2 | 10/2017 | Sholev et al. |
| 9,795,454 B2 | 10/2017 | Seeber et al. |
| 9,825,455 B2 | 11/2017 | Sandhu et al. |
| 9,877,794 B2 | 1/2018 | Csiky |
| D816,243 S | 4/2018 | Barber |
| 9,937,013 B2 | 4/2018 | Frimer et al. |
| 9,943,372 B2 | 4/2018 | Sholev et al. |
| 10,028,792 B2 | 7/2018 | Frimer et al. |
| 10,039,609 B2 | 8/2018 | Frimer et al. |
| 10,039,820 B2 | 8/2018 | Coller et al. |
| 10,052,157 B2 | 8/2018 | Frimer et al. |
| 10,064,691 B2 | 9/2018 | Frimer et al. |
| 10,071,488 B2 | 9/2018 | Robinson et al. |
| 10,085,811 B2 | 10/2018 | Weir et al. |
| 10,092,164 B2 | 10/2018 | Sholev et al. |
| 10,092,359 B2 | 10/2018 | Beira et al. |
| 10,092,365 B2 | 10/2018 | Seeber |
| 10,136,956 B2 | 11/2018 | Seeber |
| 10,201,392 B2 | 2/2019 | Frimer et al. |
| 10,265,129 B2 | 4/2019 | Beira |
| 10,325,072 B2 | 6/2019 | Beira et al. |
| 10,357,320 B2 | 7/2019 | Beira |
| 10,357,324 B2 | 7/2019 | Flatt et al. |
| 10,363,055 B2 | 7/2019 | Beira et al. |
| 10,413,374 B2 * | 9/2019 | Chassot ................ A61B 34/74 |
| 10,500,005 B2 | 12/2019 | Weir et al. |
| 10,510,447 B2 | 12/2019 | Beira et al. |
| 10,548,680 B2 | 2/2020 | Beira |
| 10,568,709 B2 | 2/2020 | Beira |
| 10,646,291 B2 | 5/2020 | Turner |
| 10,646,294 B2 | 5/2020 | Beira |
| 10,786,272 B2 | 9/2020 | Beira |
| 10,864,049 B2 | 12/2020 | Beira |
| 10,864,052 B2 | 12/2020 | Beira |
| 10,959,792 B1 | 3/2021 | Huang et al. |
| 11,020,191 B2 | 6/2021 | Diolaiti et al. |
| 11,039,820 B2 | 6/2021 | Beira |
| 11,058,503 B2 | 7/2021 | Chassot et al. |
| 11,337,716 B2 | 5/2022 | Beira |
| 11,478,315 B2 | 10/2022 | Beira |
| 11,510,745 B2 | 11/2022 | Chassot et al. |
| 11,571,195 B2 | 2/2023 | Beira |
| 11,766,301 B2 | 9/2023 | Diolaiti et al. |
| 11,844,585 B1 | 12/2023 | Friedrich et al. |
| 2001/0020200 A1 | 9/2001 | Das et al. |
| 2002/0040217 A1 | 4/2002 | Jinno |
| 2002/0049367 A1 | 4/2002 | Irion et al. |
| 2002/0072736 A1 | 6/2002 | Tierney et al. |
| 2002/0082612 A1 | 6/2002 | Moll et al. |
| 2003/0013949 A1 * | 1/2003 | Moll .................... G09B 23/285 600/407 |
| 2003/0155747 A1 | 8/2003 | Bridges |
| 2003/0208186 A1 | 11/2003 | Moreyra |
| 2004/0049205 A1 | 3/2004 | Lee et al. |
| 2004/0116906 A1 | 6/2004 | Lipow |
| 2004/0236316 A1 | 11/2004 | Danitz et al. |
| 2004/0253079 A1 | 12/2004 | Sanchez |
| 2005/0096502 A1 | 5/2005 | Khalili |
| 2005/0204851 A1 | 9/2005 | Morley et al. |
| 2005/0240078 A1 | 10/2005 | Kwon et al. |
| 2006/0043698 A1 | 3/2006 | Bridges |
| 2006/0079884 A1 | 4/2006 | Manzo et al. |
| 2006/0178559 A1 | 8/2006 | Kumar et al. |
| 2006/0183975 A1 | 8/2006 | Saadat et al. |
| 2006/0219065 A1 | 10/2006 | Jinno et al. |
| 2006/0235436 A1 | 10/2006 | Anderson et al. |
| 2006/0253109 A1 | 11/2006 | Chu |
| 2007/0088340 A1 * | 4/2007 | Brock .................... A61B 34/72 606/1 |
| 2007/0137371 A1 | 6/2007 | Devengenzo et al. |
| 2007/0156123 A1 | 7/2007 | Moll et al. |
| 2007/0208375 A1 | 9/2007 | Nishizawa et al. |
| 2007/0299387 A1 | 12/2007 | Williams et al. |
| 2008/0039255 A1 | 2/2008 | Jinno et al. |
| 2008/0046122 A1 | 2/2008 | Manzo et al. |
| 2008/0058776 A1 | 3/2008 | Jo et al. |
| 2008/0065110 A1 | 3/2008 | Duval et al. |
| 2008/0071208 A1 | 3/2008 | Voegele et al. |
| 2008/0103492 A1 | 5/2008 | Morley et al. |
| 2008/0177285 A1 * | 7/2008 | Brock .................... A61B 34/71 606/1 |

(56) References Cited

U.S. PATENT DOCUMENTS

| | | |
|---|---|---|
| 2008/0215065 A1 | 9/2008 | Wang et al. |
| 2008/0243106 A1 | 10/2008 | Coe et al. |
| 2008/0287926 A1 | 11/2008 | Abou El Kheir |
| 2008/0314181 A1 | 12/2008 | Schena |
| 2009/0030449 A1 | 1/2009 | Kawai et al. |
| 2009/0036902 A1 | 2/2009 | DiMaio et al. |
| 2009/0192522 A1 | 7/2009 | Blumenkranz |
| 2009/0198253 A1 | 8/2009 | Omori |
| 2009/0216248 A1 | 8/2009 | Uenohara et al. |
| 2009/0216249 A1 | 8/2009 | Jinno et al. |
| 2009/0247821 A1 | 10/2009 | Rogers |
| 2009/0248039 A1 | 10/2009 | Cooper et al. |
| 2009/0275994 A1 | 11/2009 | Phan et al. |
| 2009/0326552 A1 | 12/2009 | Diolaiti |
| 2010/0004508 A1 | 1/2010 | Naito et al. |
| 2010/0011900 A1 | 1/2010 | Burbank |
| 2010/0023025 A1 | 1/2010 | Zeiner et al. |
| 2010/0082041 A1 | 4/2010 | Prisco |
| 2010/0094130 A1 | 4/2010 | Ninomiya et al. |
| 2010/0121347 A1 | 5/2010 | Jaspers |
| 2010/0160929 A1 | 6/2010 | Rogers et al. |
| 2010/0160940 A1 | 6/2010 | Lutze et al. |
| 2010/0170519 A1 | 7/2010 | Romo et al. |
| 2010/0174410 A1 | 7/2010 | Greer et al. |
| 2010/0225209 A1 | 9/2010 | Goldberg et al. |
| 2010/0228249 A1 | 9/2010 | Mohr et al. |
| 2010/0234857 A1 | 9/2010 | Itkowitz et al. |
| 2010/0274087 A1 | 10/2010 | Diolaiti et al. |
| 2010/0286712 A1 | 11/2010 | Won et al. |
| 2010/0305595 A1 | 12/2010 | Hermann |
| 2010/0318099 A1 | 12/2010 | Itkowitz et al. |
| 2010/0318101 A1 | 12/2010 | Choi |
| 2010/0324551 A1 | 12/2010 | Gerhardt |
| 2010/0331859 A1 | 12/2010 | Omori |
| 2011/0071508 A1 | 3/2011 | Duval et al. |
| 2011/0087236 A1 | 4/2011 | Stokes et al. |
| 2011/0087238 A1 | 4/2011 | Wang et al. |
| 2011/0213346 A1 | 9/2011 | Morley et al. |
| 2011/0230867 A1 | 9/2011 | Hirschfeld et al. |
| 2011/0275901 A1 | 11/2011 | Shelton, IV |
| 2011/0282359 A1 | 11/2011 | Duval |
| 2011/0290854 A1* | 12/2011 | Timm ............ A61B 17/320068 227/178.1 |
| 2011/0301419 A1 | 12/2011 | Craft et al. |
| 2012/0010628 A1 | 1/2012 | Cooper et al. |
| 2012/0027762 A1 | 2/2012 | Schofield |
| 2012/0031114 A1 | 2/2012 | Mueller et al. |
| 2012/0049623 A1 | 3/2012 | Nakayama |
| 2012/0071895 A1 | 3/2012 | Stahler et al. |
| 2012/0095298 A1 | 4/2012 | Stefanchik et al. |
| 2012/0116163 A1 | 5/2012 | Lutze et al. |
| 2012/0132018 A1 | 5/2012 | Tang et al. |
| 2012/0143173 A1 | 6/2012 | Steege et al. |
| 2012/0158014 A1 | 6/2012 | Stefanchik et al. |
| 2012/0191245 A1 | 7/2012 | Fudaba et al. |
| 2012/0203269 A1 | 8/2012 | Katsuki et al. |
| 2012/0209292 A1 | 8/2012 | Devengenzo et al. |
| 2012/0232339 A1 | 9/2012 | Csiky |
| 2012/0253326 A1 | 10/2012 | Kleyman |
| 2012/0277762 A1 | 11/2012 | Lathrop et al. |
| 2012/0283745 A1 | 11/2012 | Goldberg et al. |
| 2012/0283747 A1 | 11/2012 | Popovic |
| 2012/0289973 A1 | 11/2012 | Prisco et al. |
| 2012/0289974 A1 | 11/2012 | Rogers et al. |
| 2012/0296341 A1 | 11/2012 | Seibold et al. |
| 2013/0024024 A1 | 1/2013 | Namiki |
| 2013/0123805 A1 | 5/2013 | Park et al. |
| 2013/0144274 A1 | 6/2013 | Stefanchik et al. |
| 2013/0172713 A1 | 7/2013 | Kirschenman |
| 2013/0172906 A1 | 7/2013 | Olson et al. |
| 2013/0204271 A1 | 8/2013 | Brisson et al. |
| 2013/0245643 A1 | 9/2013 | Woodard, Jr. et al. |
| 2013/0245647 A1 | 9/2013 | Martin et al. |
| 2013/0282027 A1 | 10/2013 | Woodard, Jr. et al. |
| 2013/0303408 A1 | 11/2013 | Indermuhle |
| 2013/0304083 A1 | 11/2013 | Kaercher et al. |
| 2013/0304084 A1 | 11/2013 | Beira et al. |
| 2014/0005681 A1 | 1/2014 | Gee et al. |
| 2014/0018447 A1 | 1/2014 | McGovern et al. |
| 2014/0018780 A1 | 1/2014 | Hirscheld |
| 2014/0018960 A1 | 1/2014 | Itkowitz |
| 2014/0052152 A1 | 2/2014 | Au et al. |
| 2014/0076088 A1 | 3/2014 | Berkelman et al. |
| 2014/0114481 A1 | 4/2014 | Ogawa et al. |
| 2014/0121834 A1 | 5/2014 | Ogawa et al. |
| 2014/0135794 A1 | 5/2014 | Cau |
| 2014/0142595 A1 | 5/2014 | Awtar et al. |
| 2014/0148950 A1 | 5/2014 | Ogawa et al. |
| 2014/0166023 A1 | 6/2014 | Kishi |
| 2014/0180308 A1 | 6/2014 | Von Grünberg |
| 2014/0188091 A1 | 7/2014 | Vidal et al. |
| 2014/0188159 A1 | 7/2014 | Steege |
| 2014/0195010 A1 | 7/2014 | Beira et al. |
| 2014/0200561 A1 | 7/2014 | Ingmanson et al. |
| 2014/0207150 A1 | 7/2014 | Rosa et al. |
| 2014/0229007 A1 | 8/2014 | Kishi |
| 2014/0230595 A1 | 8/2014 | Butt et al. |
| 2014/0249546 A1 | 9/2014 | Shvartsberg et al. |
| 2014/0263541 A1 | 9/2014 | Leimbach et al. |
| 2014/0263553 A1 | 9/2014 | Leimbach et al. |
| 2014/0275961 A1 | 9/2014 | Kassab et al. |
| 2014/0276950 A1 | 9/2014 | Smaby et al. |
| 2014/0276956 A1 | 9/2014 | Crainich et al. |
| 2014/0277017 A1 | 9/2014 | Leimbach et al. |
| 2014/0350570 A1 | 11/2014 | Lee |
| 2015/0057499 A1 | 2/2015 | Erden et al. |
| 2015/0057702 A1 | 2/2015 | Edmondson et al. |
| 2015/0060517 A1 | 3/2015 | Williams |
| 2015/0066018 A1 | 3/2015 | Doll et al. |
| 2015/0105821 A1 | 4/2015 | Ward et al. |
| 2015/0113933 A1 | 4/2015 | Markt |
| 2015/0142018 A1 | 5/2015 | Sniffin et al. |
| 2015/0150575 A1 | 6/2015 | Hartoumbekis et al. |
| 2015/0173840 A1 | 6/2015 | Lohmeier |
| 2015/0230869 A1 | 8/2015 | Shim et al. |
| 2015/0250547 A1 | 9/2015 | Fukushima et al. |
| 2015/0265355 A1 | 9/2015 | Prestel et al. |
| 2015/0272575 A1 | 10/2015 | Leimbach et al. |
| 2016/0022365 A1 | 1/2016 | Jensen et al. |
| 2016/0051274 A1 | 2/2016 | Howell et al. |
| 2016/0151115 A1 | 6/2016 | Karguth et al. |
| 2016/0220314 A1 | 8/2016 | Huelman et al. |
| 2016/0235486 A1 | 8/2016 | Larkin |
| 2016/0256155 A1 | 9/2016 | Shelton, IV et al. |
| 2016/0302876 A1 | 10/2016 | Teichtmann |
| 2016/0346053 A1 | 12/2016 | Beira |
| 2016/0374766 A1 | 12/2016 | Schuh |
| 2017/0020615 A1 | 1/2017 | Koenig et al. |
| 2017/0020617 A1 | 1/2017 | Weir et al. |
| 2017/0245954 A1 | 8/2017 | Beira |
| 2017/0252096 A1 | 9/2017 | Felder et al. |
| 2017/0265951 A1 | 9/2017 | Grover et al. |
| 2017/0273749 A1 | 9/2017 | Grover et al. |
| 2017/0308667 A1 | 10/2017 | Beira et al. |
| 2017/0360522 A1 | 12/2017 | Beira |
| 2017/0367778 A1 | 12/2017 | Beira |
| 2018/0000472 A1 | 1/2018 | Beira |
| 2018/0000544 A1 | 1/2018 | Beira |
| 2018/0000550 A1 | 1/2018 | Beira |
| 2018/0008358 A1 | 1/2018 | Kostrzewski et al. |
| 2018/0028269 A1 | 2/2018 | Morel et al. |
| 2018/0055583 A1 | 3/2018 | Schuh et al. |
| 2018/0078439 A1 | 3/2018 | Cagle et al. |
| 2018/0110576 A1 | 4/2018 | Kopp |
| 2018/0125519 A1 | 5/2018 | Beira et al. |
| 2018/0125592 A1 | 5/2018 | Beira |
| 2018/0242991 A1 | 8/2018 | Beira |
| 2018/0353252 A1 | 12/2018 | Chassot et al. |
| 2018/0360548 A1 | 12/2018 | Marshall et al. |
| 2019/0060012 A1 | 2/2019 | Weir et al. |
| 2019/0090969 A1 | 3/2019 | Jarc et al. |
| 2019/0133698 A1 | 5/2019 | Beira et al. |
| 2019/0175294 A1 | 6/2019 | Abbott et al. |
| 2019/0192245 A1 | 6/2019 | Abbott et al. |

(56) References Cited

U.S. PATENT DOCUMENTS

| | | |
|---|---|---|
| 2019/0239968 A1 | 8/2019 | Beira |
| 2019/0239972 A1 | 8/2019 | Chassot et al. |
| 2019/0314096 A1 | 10/2019 | Diolaiti et al. |
| 2019/0328473 A1 | 10/2019 | Chassot et al. |
| 2020/0105412 A1 | 4/2020 | Beira et al. |
| 2020/0275985 A1 | 9/2020 | Thompson et al. |
| 2020/0390510 A1 | 12/2020 | Thompson et al. |
| 2021/0093397 A1 | 4/2021 | Huang et al. |
| 2021/0307737 A1 | 10/2021 | Beira |
| 2021/0330407 A1 | 10/2021 | Chassot et al. |
| 2021/0402603 A1 | 12/2021 | Murphy et al. |
| 2023/0129956 A1 | 4/2023 | Lyons et al. |
| 2023/0142404 A1 | 5/2023 | Ariki et al. |
| 2023/0149002 A1 | 5/2023 | Beira |
| 2023/0190396 A1 | 6/2023 | Taheri et al. |
| 2023/0200629 A1 | 6/2023 | Yang et al. |

FOREIGN PATENT DOCUMENTS

| | | | |
|---|---|---|---|
| CN | 101637402 A | | 2/2010 |
| CN | 101732093 A | | 6/2010 |
| CN | 103717355 A | | 4/2014 |
| CN | 111110350 A | | 5/2020 |
| DE | 4303311 A1 | | 8/1994 |
| DE | 19652792 C2 | | 5/1999 |
| DE | 10314827 B3 | | 4/2004 |
| DE | 10314828 B3 | | 7/2004 |
| DE | 102012222755 A1 | | 6/2014 |
| DE | 102014205036 A1 | | 9/2015 |
| DE | 102014205159 A1 | | 9/2015 |
| EP | 0595291 A1 | | 5/1994 |
| EP | 0621009 A1 | | 10/1994 |
| EP | 0677275 A2 | | 10/1995 |
| EP | 0776739 A2 | | 6/1997 |
| EP | 1254642 A1 | | 11/2002 |
| EP | 1279371 B1 | | 12/2004 |
| EP | 1886630 A2 | | 2/2008 |
| EP | 1889579 A2 | | 2/2008 |
| EP | 1889583 A1 | | 2/2008 |
| EP | 2058090 A2 | | 5/2009 |
| EP | 1977677 B1 | | 8/2009 |
| EP | 2095778 A1 | | 9/2009 |
| EP | 1889583 B1 | | 4/2011 |
| EP | 2377477 B1 | | 5/2012 |
| EP | 2473119 A2 | | 7/2012 |
| EP | 2305144 B1 | | 10/2012 |
| EP | 2044893 B1 | | 7/2013 |
| EP | 2653110 A1 | | 10/2013 |
| EP | 2679192 A2 | | 1/2014 |
| EP | 2736680 A2 | | 6/2014 |
| EP | 2777536 A1 | | 9/2014 |
| EP | 2777561 A1 | | 9/2014 |
| EP | 2783643 A1 | | 10/2014 |
| EP | 2837340 A1 | | 2/2015 |
| EP | 2837354 A1 | | 2/2015 |
| EP | 2554131 B1 | | 8/2015 |
| EP | 2777561 B1 | | 10/2015 |
| EP | 2979657 A1 | | 2/2016 |
| EP | 2837340 B1 | | 10/2016 |
| EP | 2783643 B1 | | 1/2019 |
| GB | 834244 A | | 5/1960 |
| GB | 969899 A | | 9/1964 |
| JP | 2004041580 A | | 2/2004 |
| JP | 2007290096 A | | 11/2007 |
| JP | 2008104620 A | | 5/2008 |
| JP | 2009018027 A | | 1/2009 |
| KR | 20110032444 A | | 3/2011 |
| KR | 20130031403 A | | 3/2013 |
| SU | 722754 A1 | | 3/1980 |
| WO | WO-8200611 A1 | | 3/1982 |
| WO | WO-9743942 A1 | | 11/1997 |
| WO | WO-9825666 A1 | | 6/1998 |
| WO | WO-03067341 A2 | | 8/2003 |
| WO | WO-03086219 A2 | | 10/2003 |
| WO | WO-2004052171 A2 | | 6/2004 |
| WO | WO-2005009482 A2 | | 2/2005 |
| WO | WO-2005046500 A1 | | 5/2005 |
| WO | WO-2006086663 A2 | | 8/2006 |
| WO | WO-2007133065 A1 | | 11/2007 |
| WO | WO-2008130235 A2 | | 10/2008 |
| WO | WO-2009091497 A2 | | 7/2009 |
| WO | WO-2009095893 A2 | | 8/2009 |
| WO | WO-2009145572 A2 | | 12/2009 |
| WO | WO-2009157719 A2 | | 12/2009 |
| WO | WO-2010019001 A2 | | 2/2010 |
| WO | WO-2010030114 A2 | | 3/2010 |
| WO | WO-2010050771 A2 | | 5/2010 |
| WO | WO-2010083480 A2 | | 7/2010 |
| WO | WO-2010096580 A1 | | 8/2010 |
| WO | WO-2010130817 A1 | | 11/2010 |
| WO | WO-2011025818 A1 | | 3/2011 |
| WO | WO-2011027183 A2 | | 3/2011 |
| WO | WO-2011123669 A1 | | 10/2011 |
| WO | WO-2012020386 A1 | | 2/2012 |
| WO | WO-2012049623 A1 | | 4/2012 |
| WO | WO-2013007784 A1 | | 1/2013 |
| WO | WO-2013014621 A2 | | 1/2013 |
| WO | WO-2014012780 A1 | | 1/2014 |
| WO | WO-2014018447 A1 | | 1/2014 |
| WO | WO-2014067804 A1 | | 5/2014 |
| WO | WO-2014094716 A1 | | 6/2014 |
| WO | WO-2014094717 A1 | | 6/2014 |
| WO | WO-2014094718 A1 | | 6/2014 |
| WO | WO-2014094719 A1 | | 6/2014 |
| WO | WO-2014139023 A1 | | 9/2014 |
| WO | WO-2014145148 A2 | | 9/2014 |
| WO | WO-2014156221 A1 | | 10/2014 |
| WO | WO-2014201010 A1 | | 12/2014 |
| WO | WO-2014201538 A1 | | 12/2014 |
| WO | WO-2015081946 A1 | | 6/2015 |
| WO | WO-2015081947 A1 | | 6/2015 |
| WO | WO-2015088647 A1 | | 6/2015 |
| WO | WO-2015088655 A1 | | 6/2015 |
| WO | WO-2015111475 A1 | | 7/2015 |
| WO | WO-2015113933 A1 | | 8/2015 |
| WO | WO-2015129383 A1 | | 9/2015 |
| WO | WO-2015139674 A1 | | 9/2015 |
| WO | WO-2015175200 A1 | | 11/2015 |
| WO | WO-2016030767 A1 | | 3/2016 |
| WO | WO-2016083189 A1 | | 6/2016 |
| WO | WO-2016097861 A1 | | 6/2016 |
| WO | WO-2016097864 A2 | | 6/2016 |
| WO | WO-2016097868 A1 | | 6/2016 |
| WO | WO-2016097871 A1 | | 6/2016 |
| WO | WO-2016097873 A2 | | 6/2016 |
| WO | WO-2016154173 A1 | | 9/2016 |
| WO | WO-2016162751 A1 | | 10/2016 |
| WO | WO-2016162752 A1 | | 10/2016 |
| WO | WO-2016183054 A1 | | 11/2016 |
| WO | WO-2016189284 A1 | | 12/2016 |
| WO | WO-2016209891 A1 | | 12/2016 |
| WO | WO-2017015599 A1 | | 1/2017 |
| WO | WO-2017037532 A1 | | 3/2017 |
| WO | WO-2017064301 A1 | | 4/2017 |
| WO | WO-2017064303 A1 | | 4/2017 |
| WO | WO-2017064305 A1 | | 4/2017 |
| WO | WO-2017064306 A1 | | 4/2017 |
| WO | WO-2017134077 A1 | | 8/2017 |
| WO | WO-2017220978 A1 | | 12/2017 |
| WO | WO-2018142112 A1 | | 8/2018 |
| WO | WO-2018162921 A1 | | 9/2018 |
| WO | WO-2019099346 A1 | | 5/2019 |
| WO | WO-2019155383 A1 | | 8/2019 |
| WO | WO-2020026457 A1 | | 2/2020 |
| WO | WO-2020131304 A1 | | 6/2020 |
| WO | WO-2020141487 A2 | | 7/2020 |
| WO | WO-2020263870 A1 | | 12/2020 |
| WO | WO-2022175807 A1 | | 8/2022 |

OTHER PUBLICATIONS

Abbott, et al., "Design of an Endoluminal Notes Robotic System", IEEE/RSJ International Conference on Intelligent Robots and Sys-

(56) References Cited

OTHER PUBLICATIONS tems, 2007, San Diego, CA (pp. 410-416).

Aesculap Surgical Technologies, Aesculap.RTM. Caiman™, Advanced Bipolar Seal and Cut Technology Brochure, 6 pages (retrieved Aug. 31, 2015).

Arata, et al., "Development of a dexterous minimally-invasive surgical system with augmented force feedback capability", IEEE/RSJ International Conference on Intelligent Robots and Systems, 2005 (pp. 3207-3212).

Cavusoglu, et al., "Laparoscopic Telesurgical Workstation", IEEE Transactions on Robotics and Automation, (15)4:728-739 (1999).

Charles, et al., "Dexterity-enhanced Telerobotic Microsurgery", 8th International Conference Advanced Robotics, pp. 5-10 (1997).

Dachs, et al., "Novel Surgical Robot Design: Minimizing the Operating Envelope With in the Sterile Field", 28th International Conference, IEEE Engineering in Medicine Biology Society, 2006, New York (pp. 1505-1508).

Dario, et al., "Novel Mechatronic Tool for Computer-Assisted Arthroscopy," IEEE Transactions on Information Technology in Biomedicine, 4(1):15-29 (Mar. 2000).

Focacci, et al., "Lightweight Hand-held Robot for Laparoscopic Surgery", IEEE International Conference on Robotics & Automation, Rome, Italy, pp. 599-604 (2007).

Guthart, et al., The Intuitive™. "Telesurgery System: Overview and Application", IEEE International Conference on Robotics & Automation, San Francisco, CA, 2000 (pp. 618-621 ).

Ikuta, et al., "Development of Remote Microsurgery Robot and New Surgical Procedure for Deep and Narrow Space", IEEE International Conference on Robotics & Automation, Taipei, Taiwan, 2003 (pp. 1103-1108).

Ikuta, et al., "Hyper Redundant Miniature Manipulator 'Hyper Finger' for Remote Minimally Invasive Surgery in Deep Area", IEEE International Conference on Robotics & Automation, Taipei, Taiwan, 2003 (pp. 1098-1102).

Ishii, et al., "Development of a New Bending Mechanism and Its Application to Robotic Forceps Manipulator", IEEE International Conference on Robotics & Automation, Rome, Italy, 2007 (pp. 238-243).

Kobayashi, et al., "Small Occupancy Robotic Mechanisms for Endoscopic Surgery", International Conference on Medical Image Computing and Computer assisted Interventions, 2002, (pp. 75-82).

Lang, et al., "Intra-operative robotics: NeuroArm.", Acta Neurochir Suppl, 109:231-236 (2011 ).

Mayer, et al., "The Endo[PA]R System for Minimally Invasive Robotic Surgery", IEEE/RSJ International Conference on Intelligent Robots and Systems, Sendai, Japan, 2004 (pp. 3637-3642).

Mitsuishi, et al., "Development of a Remote Minimally Invasive Surgical System with Operational Environment Transmission Capability", IEEE International Conference on Robotics & Automation, Taipei, Taiwan, 2003, (pp. 2663-2670).

Mitsuishi, et al., "Master-Slave Robotic Platform and its Feasibility Study for Micro-Neurosurgery", Int. J. Med. Robot., 9(2):180-9 (2013).

Morita, et al., "Microsurgical Robotic System for the Deep Surgical Field: development of a Prototype and Feasibility Studies in Animal and Cadaveric Models", J. Neurosurg., 103(2):320-7 (2005).

Nakamura, et al., "Multi-DOF Forceps Manipulator System for Laparoscopic Surgery-Mechanism miniaturized & Evaluation of New Interface", 4th International Conference on Medical Image Computing and Computer assisted Interventions (MICCAI2001 ), 2001 (pp. 606-613).

Non-Final Office Action mailed on Jul. 14, 2023, for U.S. Appl. No. 18/167,779, filed Feb. 10, 2023, 20 pages.

Notice of Allowance mailed on Aug. 8, 2023, for U.S. Appl. No. 18/167,779, filed Feb. 10, 2023, 10 pages.

Peirs, et al., "Design of an Advanced Tool Guiding System for Robotic Surgery," IEEE International Conference on Robotics & Automation, Taipei, Taiwan, 2003, (pp. 2651-2656).

Salle, et al., "Optimal Design of High Dexterity Modular MIS Instrument for Coronary Artery Bypass Grafting", IEEE International Conference on Robotics & Automation, New Orleans, LA, 2004, (pp. 1276-1281 ).

Seibold, et al., "Prototype of Instrument for Minimally Invasive Surgery with 6-Axis Force Sensing Capability", IEEE International Conference on Robotics & Automation, Barcelona, Spain, 2005, (pp. 496-501 ).

Simaan, et al., "Dexterous System for Laryngeal Surgery: Multi-Backbone Bending Snake-like Slaves for Teleoperated Dexterous Surgical Tool Manipulation", IEEE International Conference on Robotics & Automation, New Orleans, LA, 2004 (pp. 351-357).

Stryker™, Endoscopy, Take a Look Around, Ideal Eyes.TM. FFD122 HD, Articulating Laparoscope Brochure, 2 pages (2009).

Tavakoli, et al., "Force Reflective Master-Slave System for Minimally Invasive Surgery", IEEE/RSJ International Conference on Intelligent Robots and Systems, Las Vegas, NV, 2003, (pp. 3077-3082).

Taylor, et al., "Steady-Hand Robotic System for Microsurgical Augmentation", The International Journal of Robotics Research, 18(12):1201-1210 (1999).

www.cttc.co/technologies/maestro-non-robotic-dexterous-laproscopic-instrum-ent-writsproviding-seven-degrees, Maestro: Non-Robotic Dexterous Laproscopic Instrument With a Wrist Providing Seven Degrees of Freedom, accessed Nov. 12, 2015, 4 pages.

Yamashita, et al., "Development of Endoscopic Forceps Manipulator Using Multi-Slider Linkage Mechanisms", The 1st Asian Symposium on Computer Aided Surgery-Robotic and Image-Guided Surgery, Ibaraki, Japan, 4 pages (2005).

Zeus, Robotic Surgical System, available at http://allaboutroboticsurgery.com/zeusrobot.html. (2017) 4 pages.

Notice of Allowance mailed on Jan. 31, 2024, for U.S. Appl. No. 18/504,087, filed Nov. 7, 2023, 12 pages.

Invitation to pay additional fees for International Application No. PCT/EP2024/053361 dated Apr. 29, 2024, 22 pages.

International Search Report and Written Opinion mailed on Jun. 19, 2024, for International Application No. PCT/EP2024/053361, 31 pages.

* cited by examiner

SURGICAL ROBOTICS SYSTEMS AND DEVICES HAVING A STERILE RESTART, AND METHODS THEREOF

CROSS-REFERENCE TO RELATED APPLICATION

This is a continuation of U.S. patent application Ser. No. 18/167,779, filed Feb. 10, 2023, now U.S. Pat. No. 11,844,585, the contents of which are incorporated herein by reference.

TECHNICAL FIELD

This application generally relates to surgical robot systems, and specifically to systems, devices, and methods for restarting a surgical robotic system without comprising sterility.

BACKGROUND

In robotically-assisted or tele-manipulated surgical robotic systems, a surgeon operates a master console to remotely control one or more slave devices or surgical instruments at a surgical site. During the operation of the surgical robotic system, there may be events or factors that cause unexpected movement and/or operation of one or more components of the system. In these instances, a surgical robotic system may transition into a safe operating mode, whereby one or more functions of the surgical robotic system may be disabled. To restart the surgical robotic device, a surgeon or other user within an operating room may need to perform one or more actions that may compromise a sterile field. In some cases, the surgeon or other user may also need to release one or more surgical instruments from a patient before initiating a restart. If the sterile field is compromised either during an instrument release or restart of the surgical robotic system, then significant delays may result in a surgical procedure. As such, it may be desirable to have a way to restart a surgical robotic system without comprising the sterile field.

BRIEF DESCRIPTION

The present disclosure overcomes the drawbacks of previously-known surgical robotic systems by providing systems, devices, and methods for restarting a surgical robotic system without comprising sterility of a surgical site.

In some embodiments, an apparatus can include: a restart of a surgical robotic system that is configured to be activated by a sterile user from within a sterile field without compromising the sterile field; and a controller operatively coupled to the restart, the controller configured to: detect that the restart has been activated; and in response to detecting that the restart has been activated, restart the surgical robotic system.

In some embodiments, an apparatus can include: a restart of a surgical robotic system that is configured to be activated by a user from within a sterile field without compromising the sterile field; and a controller operatively coupled to the restart, the controller configured to: detect that the restart has been activated; in response to detecting that the restart has been activated, determine whether an instrument is coupled to a slave manipulator of the surgical robotic system; and in response to determining that the instrument is in the active state, enabling telemanipulation of the instrument in a predefined set of degrees-of-freedom (DOFs) that allows the instrument to engage further with or disengage from tissue or other components within a body of a patient without compromising the sterile field.

In some embodiments, a system can include: at least one slave manipulator isolated from a sterile field by a first sterile barrier, the at least one slave manipulator including a plurality of slave links and a plurality of drive units; at least one instrument configured to be removably coupled to the at least one slave manipulator, the at least one sterile instrument configured to be positioned via movement of the plurality of slave links and to be manipulated in a plurality of degrees-of-freedom (DOFs) via activation of the plurality of drive units; and a master console disposed separately from the slave manipulator and isolated from the sterile field by a second sterile barrier, the master console including a plurality of master links being operatively coupled to the plurality of slave links such that movement of the plurality of master links causes corresponding movement in the plurality of slave links; at least one sterile handle grip configured to be removably coupled to the master console, the at least one sterile handle grip when coupled to the master console being configured to control the activation of the plurality of drive units to manipulate the at least one instrument in the plurality of DOFs; a restart that is configured to be activated by a user from within the sterile field without compromising the sterile field; and at least one controller operatively coupled to the at least one slave manipulator and the master console, the controller configured to: deactivate controlled movement of the plurality of slave links and the manipulation of at least one instrument during a surgical procedure in response to detecting an abnormal event; detect that the restart has been activated; and after detecting that the restart has been activated, restart the surgical robotic system.

In some embodiments, a method for maintaining sterility of a surgical robotic system while restarting during a surgical procedure can include: after the interruption and with a slave manipulator of the surgical robotic system being deactivated from movement, detecting that a restart of the surgical robotic system that is configured to be activated from within a sterile field and without compromising sterility has been activated; and after detecting that the restart has been activated, restarting the surgical robotic system.

DETAILED DESCRIPTION

The present disclosure relates to surgical robotic systems having a master console and slave manipulators, with components and features for enabling a restart without comprising the sterility of the surgical robotic system. Systems, devices, and methods described herein allow a surgical robotic system to be restarted as well as an instrument to be released (or to perform other functions) after a temporary interruption, while maintaining a sterile environment.

During a surgical operation, a surgical robotic system may be used to perform certain minimally invasive procedures. In some embodiments, the surgical robotic system may include one or more patient-side carts and a surgeon or master console. The patient-side carts may include manipulators (e.g., robotic arms) that support one or more sterile instruments, which may be used during the surgical operation to engage with the patient anatomy. At times, it may become necessary to restart the surgical robotic system. For example, the surgical robotic system may experience a temporary interruption if certain events and/or conditions arise (e.g., unexpected movement, collisions, component failure). When there is a temporary interruption, the surgical robotic system may disable certain functions (e.g., deactivate movement of the slave manipulators and/or sterile instruments). To then resume the surgical robotic operation, the surgical robotic system may need to be restarted and/or any instruments coupled to the surgical robotic system may need to be released from the patient anatomy.

Figure 1:
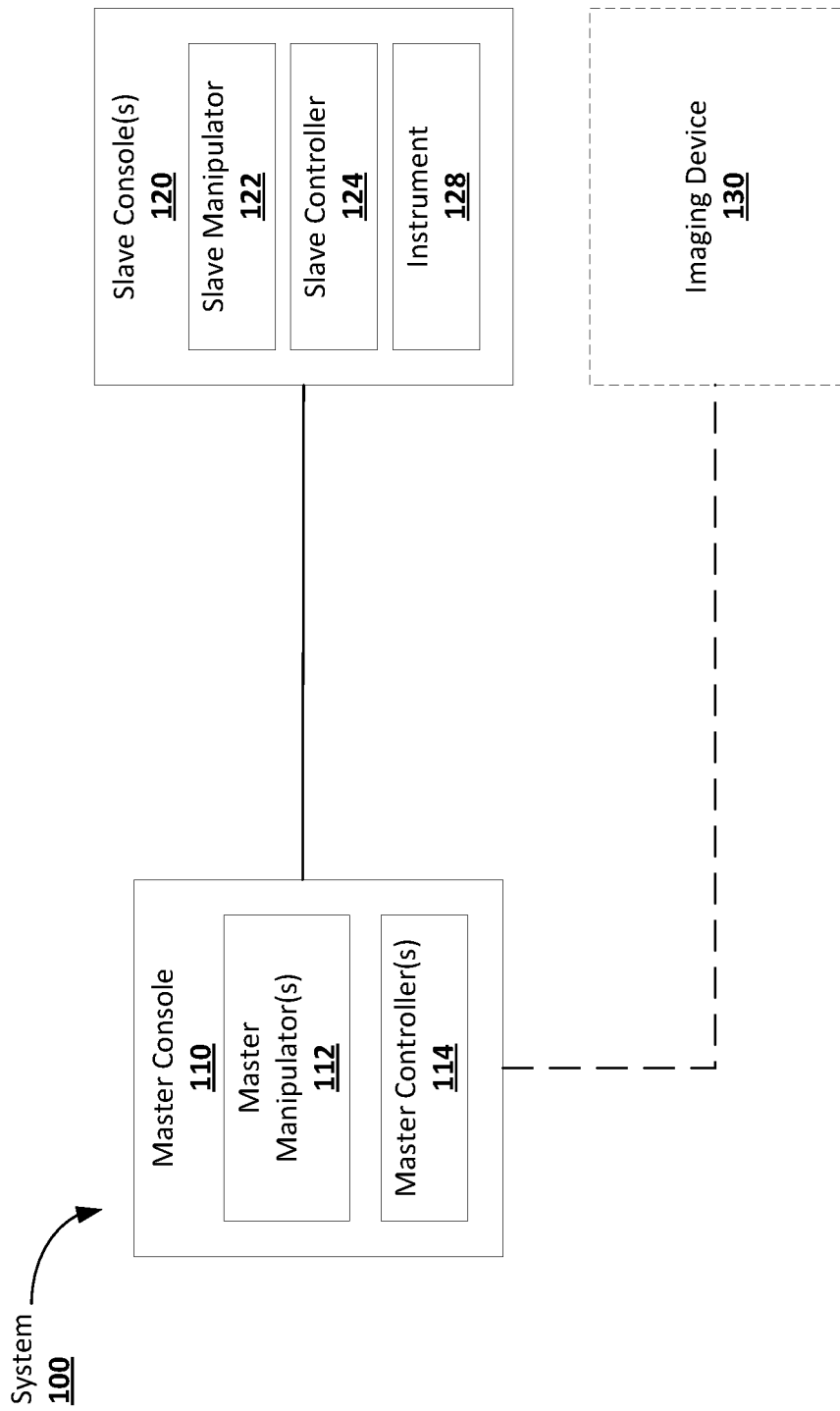
FIG. 1 schematically depicts a surgical robotic system, according to embodiments.

FIG. 1 schematically depicts a surgical robotic system 100, according to embodiments. The system 100 can include a master console 110 and one or more slave console(s) 120. Optionally, the system 100 can also include an imaging device 130, such as, for example, an endoscopic camera.

The master console 110 can be operatively coupled to the slave console(s) 120. For example, the master console 110 can be coupled to the slave console(s) 120 via wired and/or wireless connections. The master console 110 can include one or more master manipulator(s) 112 and one or more master controller(s) 114. The master manipulator(s) 112 can include a plurality of master links that are interconnected by a plurality of joints. Movement can be applied to the master manipulator(s) 112 by a sterile handle, which can be actuated by a sterile user (e.g., a surgeon). The movement of the master manipulator(s) 112 and one or more actuators of the handle can be sensed, e.g., using a plurality of sensors, and transmitted to the master controller(s) 114. In operation, the master controller(s) 114 can send instructions to one or more slave console(s) 120 to cause one or more drive units and/or actuators at the slave console(s) 120 to move based on the movements applied at the master console 110.

Each slave console 120 can include a slave manipulator 122 and/or an instrument 128 that is coupled to the slave manipulator 122. The slave manipulator 122 can include a plurality of links that are interconnected by a plurality of joints, and the instrument 128 can include one or more components that can be actuated in a plurality of degrees of freedom (DOFs). The slave console(s) 120 can include one or more drive units and/or actuators that control movement of the plurality of links and joints of the slave manipulator 122 and the component(s) of the instrument 128. In accordance with aspects of the present disclosures, the slave manipulator 112 and the instrument 128 of the slave console (s) 120 can be configured to move in a manner responsive to movements applied at the handle of the master console 110, such that the slave manipulator 112 and the instrument 128 reproduces the movement applied at the handle of the master console 110. In particular, the master console 110 can generate instructions or commands based on movements applied at the handle and transmit those instructions or commands to the slave console(s) 120 to cause movement of the slave manipulator 112 and/or the instrument 128. The slave console(s) 120 can include a slave controller 124 that can be configured to interpret the instructions or other signals from the master console 110 and to control the movement of the slave manipulator 112 and/or the instrument 128.

While the slave console 120 is described as having a slave manipulator 122 and an instrument 128, it can be appreciated that a single slave console 120 can include more than one slave manipulator 122 and/or more than one instrument 128. For example, a slave console 120 can include two slave manipulators 122 that each support one or more instruments 128.

The master controller(s) 114 and the slave controller(s) 124, as described herein, can include one or more of a memory, a processor, a communications interface, and/or an input/output device. The memory can include any type of suitable non-transitory compute readable media that can store instructions that can be executed by one or more processors. The memory can be, for example, a random access memory (RAM), a memory buffer, a hard drive, a database, an erasable programmable read-only memory (EPROM), an electrically erasable read-only memory (EEPROM), a read-only memory (ROM), and/or so forth. The processor can be any suitable processing device configured to run and/or execute functions associated with the surgical robotic system 100. The processor can be a general purpose processor, a Field Programmable Gate Array (FPGA), an Application Specific Integrated Circuit (ASIC), a Digital Signal Processor (DSP), and/or the like. The communications interface can include wired and/or wireless interfaces for receiving information and/or sending information to other devices. The input/output device can include one or more displays, audio devices, touchscreens, keyboards, or other input or output devices for presenting information to and/or receiving information from a user.

Further examples of surgical robotic systems are described in PCT Patent Application No. PCT/IB2020/050039, filed Jan. 4, 2020, titled "Surgical Robot Systems Comprising Robotic Telemanipulators and Integrated Laparoscopy." and U.S. patent application Ser. No. 16/269,383, filed Feb. 6, 2019, titled "Surgical Robot Systems Comprising Robotic Telemanipulators and Integrated Laparoscopy," the disclosures of each of which are incorporated by reference herein.

Figure 2:
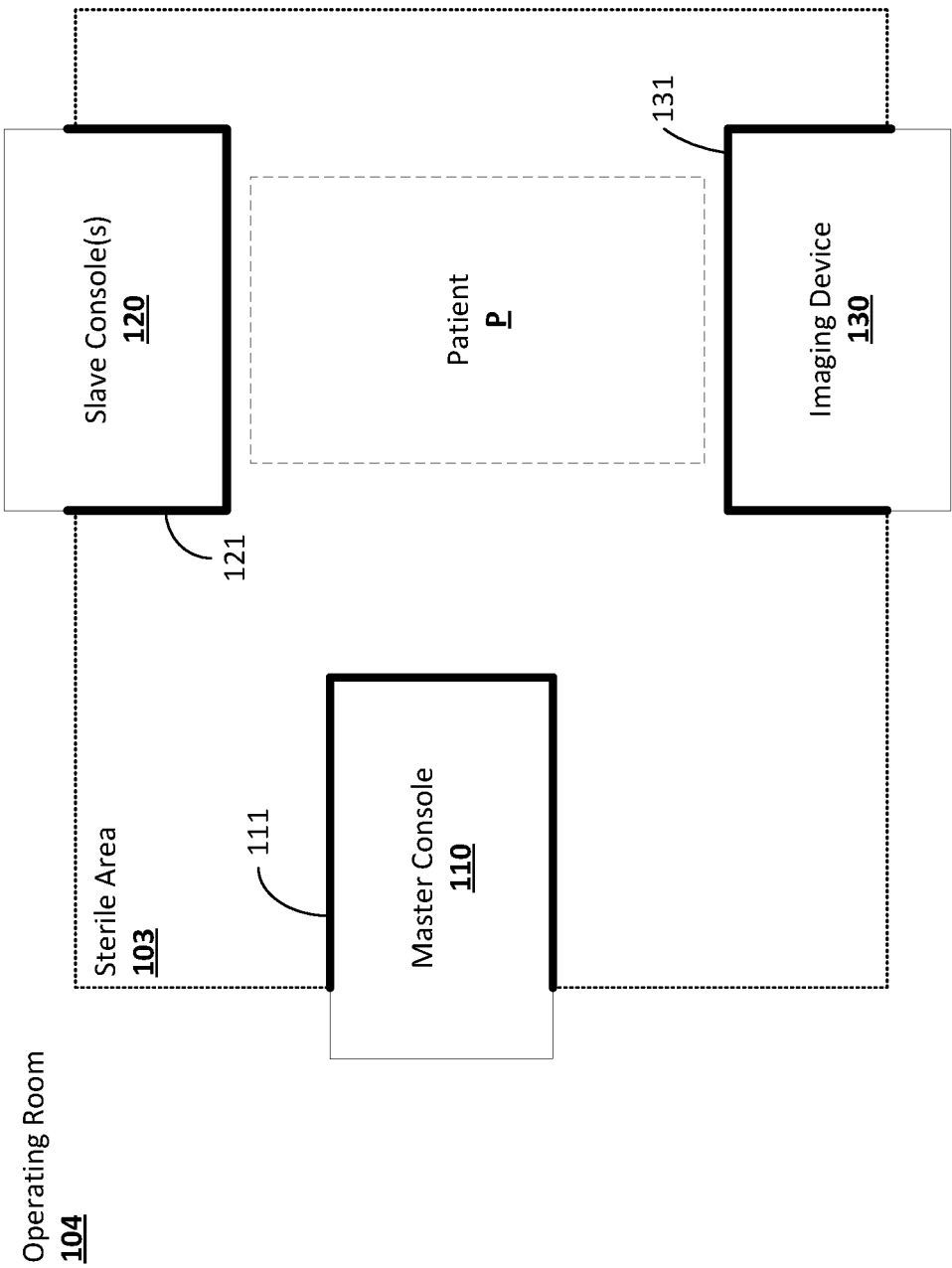
FIG. 2 schematically depicts a surgical robotic system in an environment around a sterile area, according to embodiments.

FIG. 2 depicts the master console 110, the slave console (s) 120, and the imaging device 130 in an operating room 104, including a sterile area 103, according to embodiments. The master console 110, the slave console(s) 120, and the imaging device 130 can be designed to remain sterile during a surgical operation.

As depicted, the master console 110 can be located within the operating room 104. The master console 110 can include a portion that covered by one or more sterile drape(s) 111, which allows that portion of the master console 110 to remain sterile during a surgical operation. In some embodiments, the master manipulator(s) 112 and the master controller(s) 114 can be covered by one or more sterile drape(s) 111, while certain sterile components (e.g., handles) can be removably coupled to the master manipulator at sterile coupling interfaces.

The slave console(s) 120 can be located within the operating room 104 and distributed around a patient P. Each slave console 120 can include a portion that is covered by one or more sterile drapes 121, which allows that portion of the respective slave console 120 to remain sterile during the surgical operation. The slave console(s) 120 can be configured to support and manipulate one or more surgical instruments. The surgical instruments can be sterile, and can be removably coupled to the slave console(s) 120 via sterile coupling interfaces.

If the system 100 includes an imaging device 130, then the imaging device 130 can also include a portion that is covered by one or more sterile drapes 131, which allows that portion of the imaging device 130 to remain sterile during a surgical operation.

While one or more controllers are described with reference to FIGS. 1 and 2, it can be appreciated that any functions implemented by one controller can be implemented by one or more controllers, and that the recitation of "a controller" is not limited to that of a single controller but can encompass one or more controllers.

Figure 3:
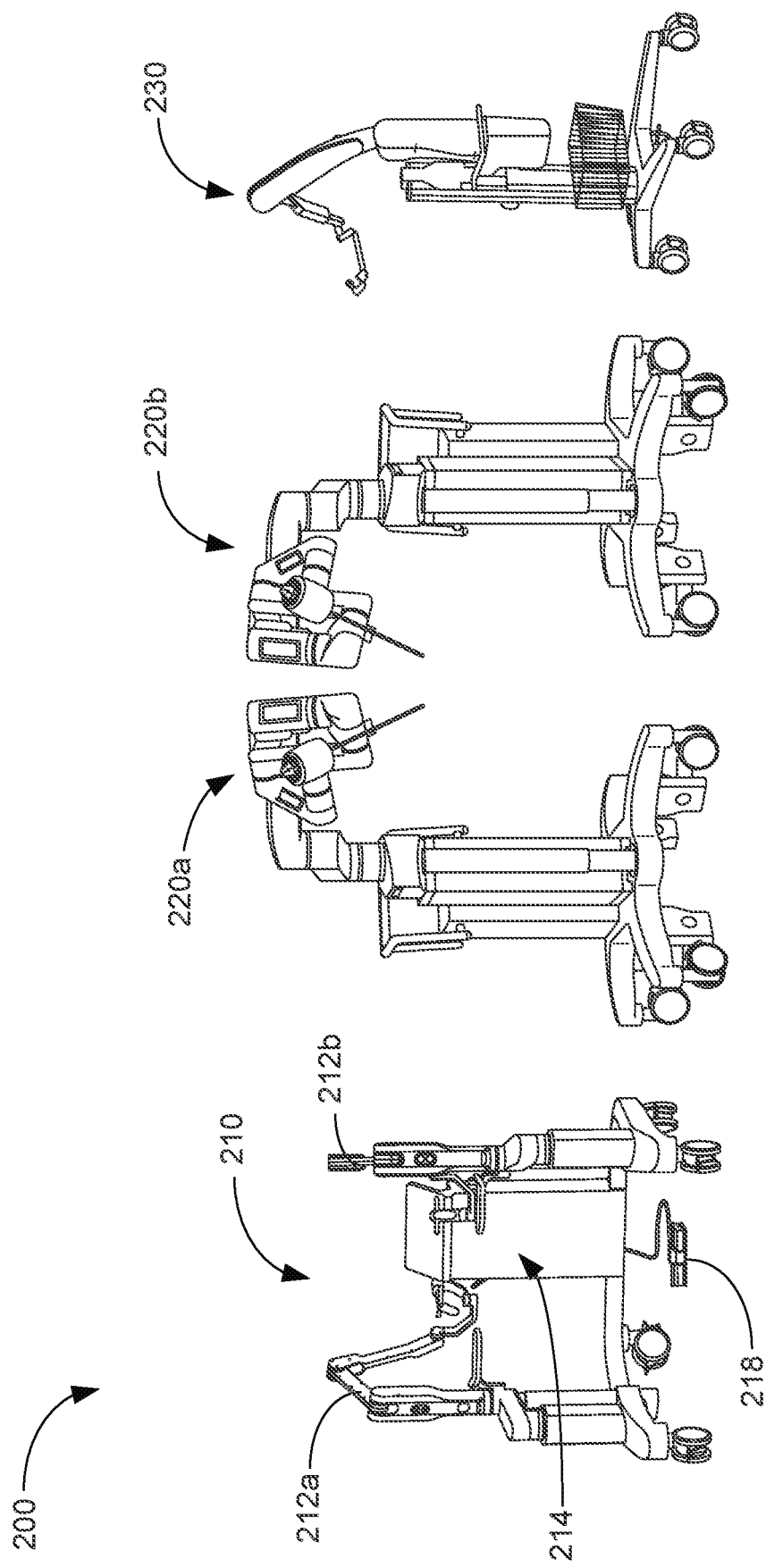
FIG. 3 shows an example surgical robotic system including a master console and multiple slave manipulators, according to embodiments.

FIG. 3 depicts an example of a surgical robotic system 200, according to embodiments. The surgical robotic system 200 can be structurally and/or functionally similar to other surgical robotic systems described herein, including, for example, the surgical robotic system 100, and therefore can include components that are structurally and/or functionally similar to the components of such other systems. For example, the surgical robotic system 200 can include a master console 210 including two master manipulators 212a and 212b (e.g., left and right manipulators) and a master controller 214, two slave consoles 220a, 220b (e.g., left and right slave consoles), and an imaging device implemented as an endoscope device 230.

In operation, movement of the first slave manipulator 212a (and handle coupled thereto) can be sensed and transmitted to the master controller 214, which can then send instructions to a first slave console 220a to control the movement of the first slave console 220a. Similarly, movement of the second slave manipulator 212b (and handle coupled thereto) can be sensed and transmitted to the master controller 214, which can then send instructions to a second slave console 220b to control the movement of the second slave console 220b. In some embodiments, the master console 210 can also include one or more foot pedal(s) or other actuator(s), which can be depressed to engage or release a clutch. When the clutch is engaged (e.g., by depressing the one or more foot pedal(s)), the master controller 214 can be configured to send instructions that cause the slave consoles 220a, 220b to replicate movements of the master manipulators 212a, 212b. And when the clutch is not engaged, the master controller 214 may pause sending instruction to the slave consoles 220a, 220b, such that the slave consoles 220a, 220b do not replicate the movements of the master manipulators 212a, 212b and/or deactivate the movement of the slave console(s) 220a, 220b in some other manner.

Figure 4:
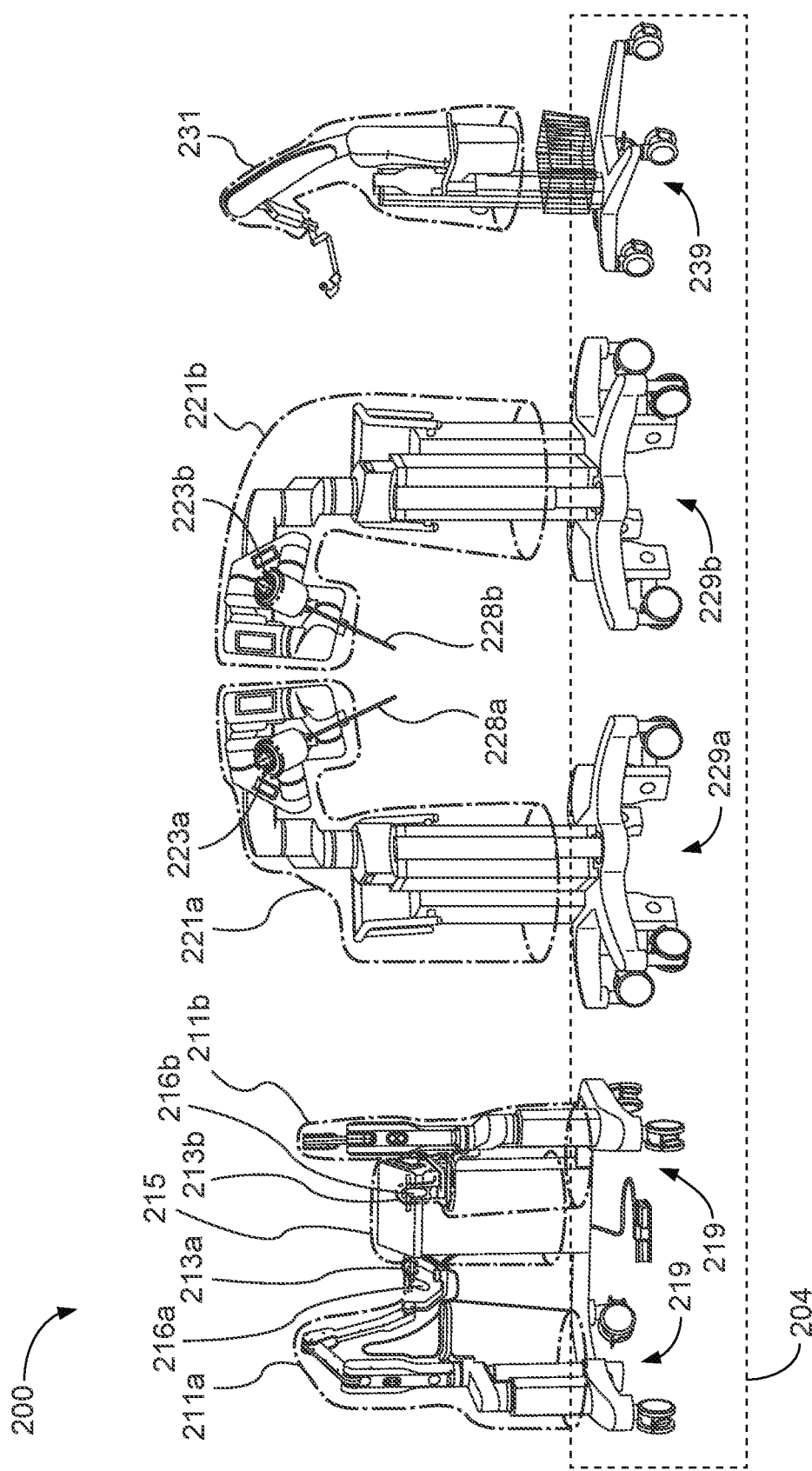
FIG. 4 depicts the sterile zones around the example surgical robotic system of FIG. 3, according to embodiments.

FIG. 4 depicts the sterile zones or regions of the surgical robotic system 200, according to embodiments. As shown, the master console can include a first sterile zone 211a, a second sterile zone 211b, and a third sterile zone 215. The first sterile zone 211a can cover the first master manipulator 212a (e.g., a left master manipulator), and the second sterile zone 211b can cover the second master manipulator 212b (e.g., a right master manipulator). A first sterile handle 216a can be removably coupled to the first master manipulator 212a at a first sterile coupling interface 213a, and a second sterile handle 216b can be removably coupled to the second master manipulator 212b at a second sterile coupling interface 213b. The third sterile zone 215 can cover a master controller and/or display unit. The master console 210 can also include components or surfaces 219 outside of the first, second and third sterile zones 211a, 211b, 215 that are disposed in a non-sterile zone 204. For example, the master console 210 can include one or more transport elements (e.g., wheels) and foot pedals 218 that are disposed outside of the sterile zones 211a, 211b, 215.

A first slave console 220a (e.g., a left slave console) may include a sterile zone 221a (e.g., a fourth sterile zone). A sterile instrument 228a can be removably couplable to the first slave console 220a (and specifically, a slave manipulator of the first slave console 220a) at a sterile coupling interface 223a. The sterile coupling interface 223a can allow the sterile instrument 228a to be coupled to and decoupled from the first slave console 220a without compromising the sterile zone 221a of the first slave console 220a. A second slave console 220b (e.g., a right slave console) may include a sterile zone 220b (e.g., a fifth sterile zone). A sterile instrument 228b can be removably couplable to the second slave console 220b (and specifically, a slave manipulator of the second slave console 220b) at a sterile coupling interface 223b. The sterile coupling interface 228b can allow the sterile instrument 228b to be coupled to and decoupled from the second slave console 220b without compromising the sterile zone 221b of the second slave console 220b. The first and second slave consoles 220a, 220b can also include components or surfaces 229a, 229b, respectively, that are disposed outside of the sterile zones 221a, 221b. For example, the slave consoles 220a, 220b can include one or more transport elements 229a, 229b (e.g., wheels) that are disposed outside of the sterile zones 221a, 221b.

The endoscopic device 230 can include a sterile zone 231 (e.g., a sixth sterile zone) and one or more non-sterile components or surfaces 239.

Figure 5:
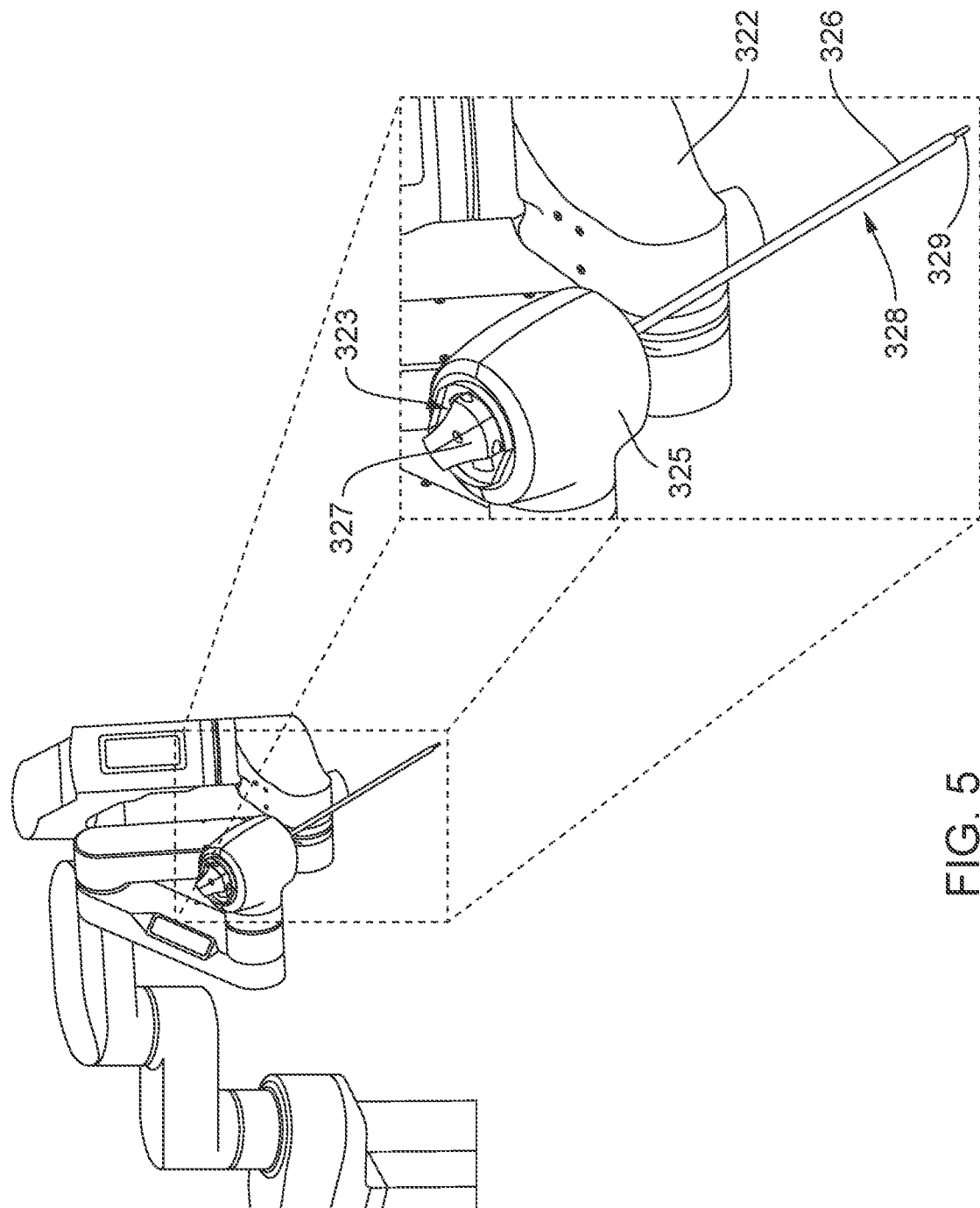
FIG. 5 depicts a detailed view of an instrument coupling of a surgical robotic system, according to embodiments.

FIG. 5 provides a more detailed view of an instrument 328 and an instrument coupling interface 323 of a surgical robotic system, according to embodiments. The instrument 328 can be structurally and/or functionally similar to other instruments described herein (e.g., instruments 228a, 228b), and the coupling interface 323 can be structurally and/or functionally similar to other coupling interfaces described herein (e.g., coupling interfaces 223a, 223b).

As shown in FIG. 5, the instrument 328 can be coupled to a slave manipulator 322 of a slave console. The slave manipulator 322 can include a plurality of links interconnected by a plurality of joints. The slave manipulator 322 can terminate at an instrument hub 325, which can define an opening through which the instrument 328 can be received. The slave manipulator 322 and the instrument hub 325 can be non-sterile components of the surgical robotic system and therefore be covered by a sterile drape during a surgical operation. To maintain sterility while coupling and uncoupling a sterile instrument to the slave manipulator 322, a sterile coupling interface 323 can be coupled to the instrument hub 325. In particular, the sterile coupling interface 323 can be inserted within the opening of the instrument hub 325 and provide an interface for engaging with the instrument 328. The sterile coupling interface 323 can define a lumen or opening for receiving the instrument 328.

The instrument 328 can include a head 327 at a proximal region of the instrument 328, an end effector 329 at a distal region of the instrument, and a shaft 326 extending therebetween. The head 327 and/or shaft 326 can define one or more lumens, e.g., for receiving one or more other components such as, for example, electrical cables for coupling an electrosurgical generator with the end effector 329 and/or cables for actuating the end effector 329. The instrument 328 can be sized and shaped to be inserted through the lumen or opening of the sterile coupling interface 323. Further examples of instruments and coupling interfaces are described in U.S. patent application Ser. No. 15/976,812, filed May 10, 2018, titled "Translational Instrument Interface for Surgical Robot and Surgical Robot Systems Comprising the Same," the disclosure of which is incorporated herein by reference.

Figure 6:
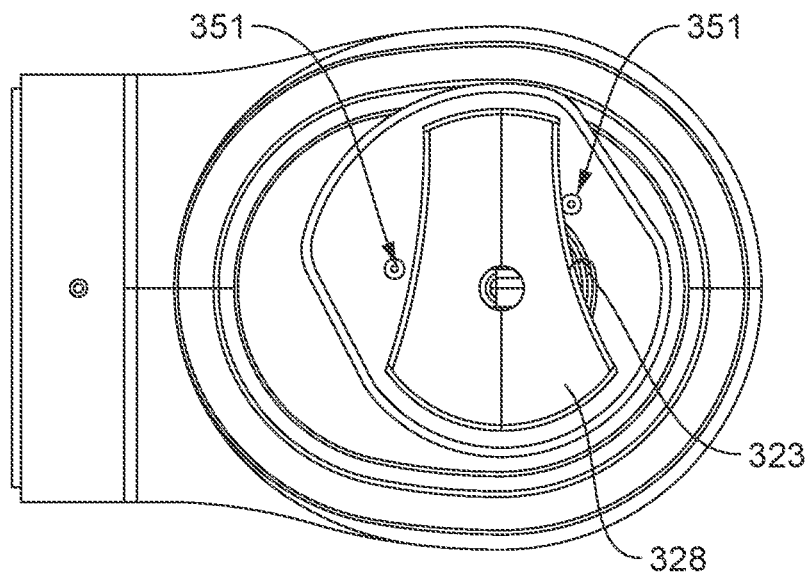
FIG. 6 depicts the sterile boundary around the instrument coupling of a surgical robotic system, according to embodiments.

FIG. 6 provides a detailed view of the proximal side of the instrument 328 when inserted within the sterile coupling interface 323, according to embodiments. When the instrument 328 is received within the sterile coupling interface 323, the instrument 328 can be coupled to one or more drive units and/or actuators of the slave console. The one or more drive units and/or actuators of the slave console can then control movement of the end effector 329 in one or more DOFs. In some embodiments, the one or more actuators can include linear actuators that can translate to actuate movement of the end effector 329 in a plurality of DOFs.

During a surgical operation, the one or more drive units and/or actuators of the slave console may drive movement of the end effector 329 of the instrument 328 to perform a surgical task, such as, for example, grasping tissue and/or gripping a needle, suture or other object. When the surgical operation is interrupted, e.g., due to a non-critical temporary interruption, the surgical robotic system may not be easily restarted if the instrument 328 (or other instruments coupled to the surgical robotic system) is blocked inside of the patient (e.g., grasped onto patient tissue and/or gripped onto a needle, suture, or other object). In these instances, the instrument 328 may need to be released first (e.g., released from the tissue, needle, or suture) under controlled conditions before surgical robotic system can be restarted. If the instrument 328 is blocked inside of the patient while tissue is grasped, uncontrolled motion to release the instrument may cause damages to the patient.

Figure 7:
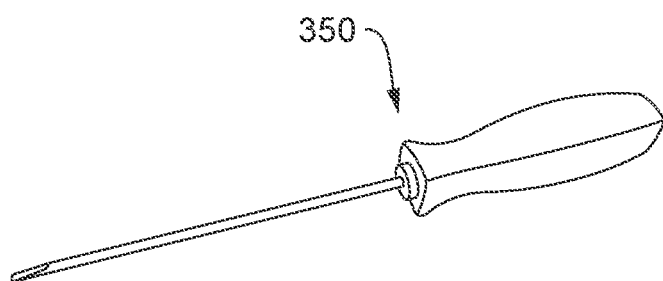
FIG. 7 depicts an emergency release tool for releasing an instrument of a surgical robotic system, according to embodiments.

In some embodiments, the surgical robotic system may include one or more emergency release features 351. The emergency release features 351 may be cavities that can receive an emergency release tool, such as the tool 350 shown in FIG. 7. The tool 350 can be inserted into the cavities to allow one or more actuators of the instrument 328 to move to release the end effector 329. As depicted in FIG. 7, the emergency release tool 350 can be a screwdriver with a tip sized and shaped for insertion into the cavities. While a screwdriver is depicted, it can be appreciated that any elongate member or shaft that has an end shaped to be inserted into the cavities can be used to release the instrument 328. While the emergency release tool 350 may provide a way to release the instrument 328, the use of the emergency release tool 350 may compromise the sterility of the surgical robotic system. In particular, the emergency release features 351 may be disposed on the slave manipulator 322 and/or sterile interface 323 behind a surgical drape. Therefore, when the emergency release tool 350 is inserted into the cavities, the tool 350 may breach the sterile barrier and compromise the sterility of the surgical robotic system. To resume the surgical operation, sterility would then need to be restored by exchanging the sterile coupling interface 323 and the sterile drape, which can lead to significant delays. In some instances, when multiple instruments 328 coupled to multiple slave consoles are locked within the patient, the use of the emergency release tool 350 at each of the slave consoles would require sterility to be restored at each of the slave consoles before the surgical operation can be resumed. As such, an improved instrument release procedure that does not compromise the sterility of the surgical robotic system may be desired, as further described below.

Figure 8:
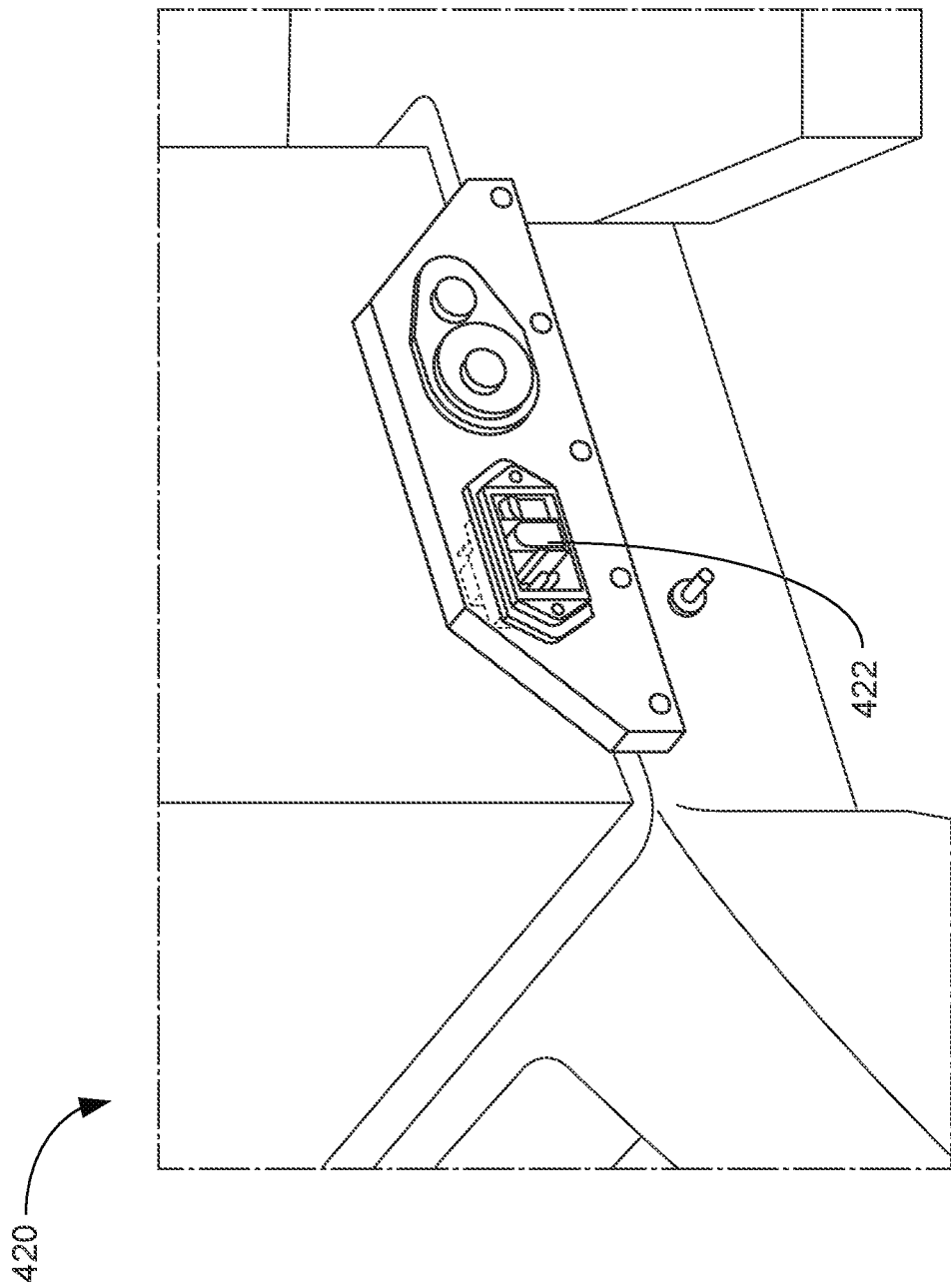
FIG. 8 depicts a power supply switch of a slave manipulator of a surgical robotic system, according to embodiments.

After an unexpected interruption, it may also be necessary to restart the various components of the surgical robotic system before resuming the surgical operation. For example, each of the slave consoles that are in use may need to be restarted before the surgical operation can resume. In some embodiments, a slave console can include a switch or other actuator for restarting. For example, as depicted in FIG. 8, a slave console 420 may include a power supply switch 422 that can be manually actuated, e.g., by a user, to restart the slave console 420. In particular, actuating the power supply switch 422 can cycle power off and on to the slave console 420. The switch 422, however, may be difficult for a user to access. Due to space constraints within an operating room and/or to avoid accidental actuation of the switch, the switch 422 may need to be placed at a location that is more concealed or secluded location. In some embodiments, the switch 422 may also be placed at a non-sterile location, e.g., near a bottom of the slave console 420. While the switch 422 at this location is unlikely to be accidentally actuated and is out of the way of other moving components of the slave console 420, actuation of the switch 422 may compromise the sterility of the user and necessitate a new sterile setup. Such can lead to significant delays before the surgical operation can be resumed. As such, an improved restart procedure that is easier to initiate and does not compromise the sterility of the surgical robotic system may be desired, as further described below.

Systems, devices, and methods described herein provide mechanisms for restarting a surgical robotic system and/or releasing one or more surgical instruments without compromising sterility. The restart procedure can be initiated or performed from a sterile area of a surgical robotic system. If any instruments are blocked within a patient, then the restart procedure can include or be followed by an instrument release procedure, whereby an instrument can be actuated to release from patient tissue and/or other objects within a patient without compromising the sterility of the surgical robotic system and/or components and accessories thereof or the sterility of users within the operating room.

Figure 9:
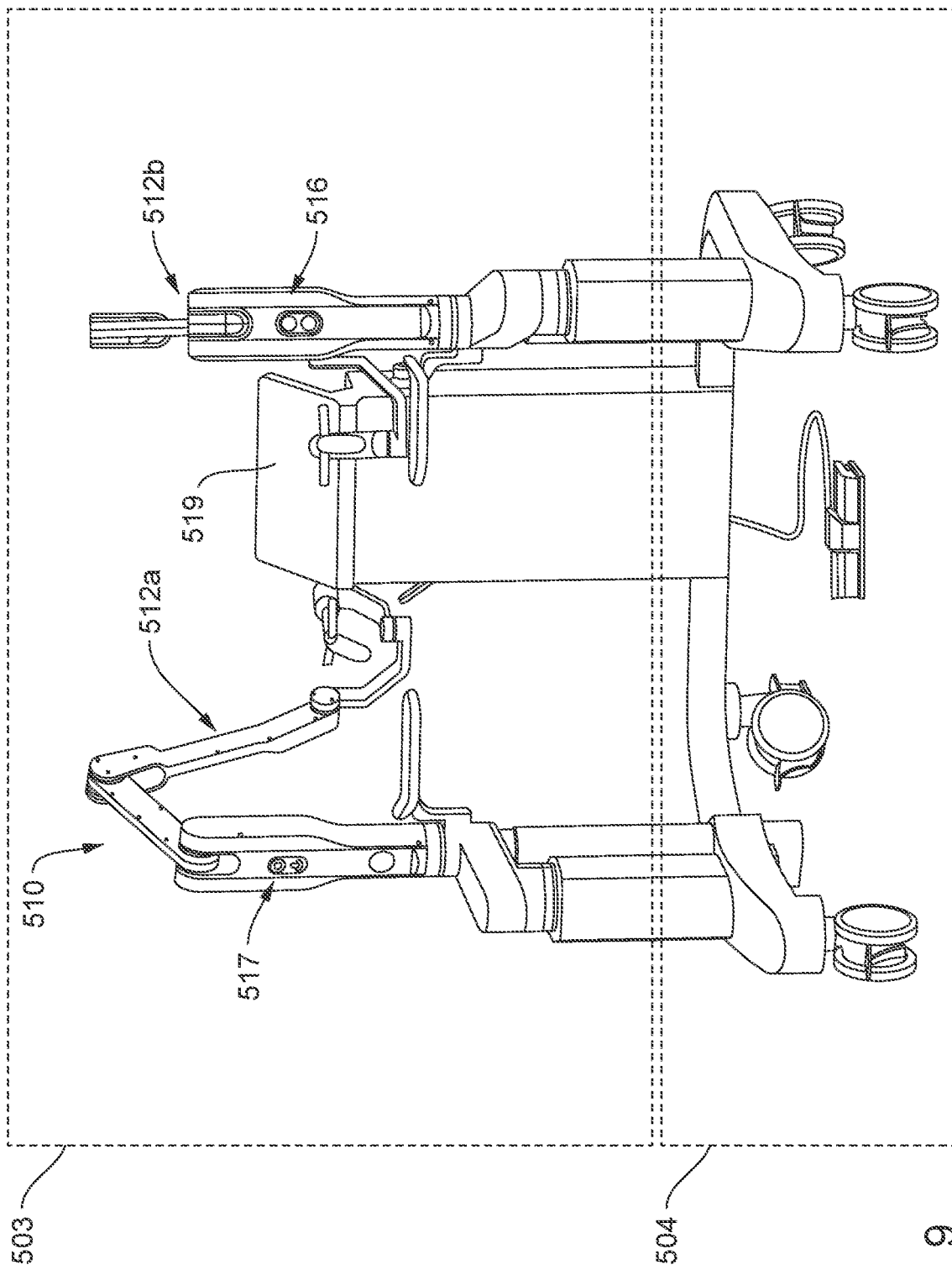
FIG. 9 depicts the sterile and non-sterile zones around a master console of a surgical robotic system, according to embodiments.

FIG. 9 depicts an example master console 510 of a surgical robotic system, where the master console 510 includes functions for implementing a restart procedure, according to embodiments. The master console 510 can be structurally and/or functionally similar to other master consoles described herein, including, for example, master console 110, 210, etc. For example, the master console 510 can include a first master manipulator 512a (e.g., a left master manipulator), a second master manipulator 512b (e.g., a right master manipulator), and a display 519. The master console 510 can also include a restart. The restart can be implemented as one or more physical actuators, such as one or more buttons, switches, sliders, pedals, knobs, wheels, etc. As depicted in FIG. 9 in greater detail in FIG. 10, the master console 510 can include two sets of buttons 516, 517. The set of buttons 516 can include two buttons 516a, 516b, and the set of buttons 517 can include a single button. Alternatively, or additionally, the restart can be implemented as a virtual element, such as, for example, a virtual button, a virtual slider, a virtual switch, etc. The virtual element can be presented to a user via a display, e.g., display 519. Still alternatively, or additionally, the restart can be implemented via audio recognition (e.g., by a user speaking a specific command to a microphone), gesture recognition (e.g., by a user gesturing to an image capture device), or the like.

Importantly, the restart can be activated or actuated by a sterile user within the sterile field without comprising sterility. In the example depicted in FIG. 9, the restart implemented as one or more sets of buttons 516, 517 is located within a sterile zone or region 503 of the master console 510. The sterile zone 503 can be established using one or more surgical drapes, e.g., similar to that described above with reference to FIG. 4. Surgical drapes, however, typically do not extend to the floor of an operating room, and therefore at least a region 504 of the master console 510 may remain un-draped and therefore non-sterile. The one or more buttons 516, 517 can be located on the master console 510 in the sterile zone 503 such that a user can actuate or activate the sets of buttons 516, 517 without compromising sterility. For example, a user can press or push on one or more buttons from the sets of buttons 516, 517 through the sterile drape without breaching (e.g., breaking or damaging) the sterile drape. Therefore, when the surgical robotic system is temporarily interrupted and requires a restart, a sterile operator (e.g., surgeon or other user) can restart the surgical robotic system by pressing one or more buttons from the sets of buttons 516, 517.

In some embodiments, the sets of buttons 516, 517 may need to be pressed according to a predefined combination or sequence before activating a restart. For example, one or more buttons may need to be pressed concurrently or sequentially for a predefined period of time (e.g., between about 2 seconds and about 10 seconds, inclusive of all sub-ranges and values) to activate the restart. In some embodiments, a single button may need to be pressed for a predefined period of time (e.g., between about 2 seconds and about 10 seconds, inclusive of all sub-ranges and values) to activate the restart. Having a specific combination or sequence can avoid an accidental restart. In some embodiments, activation of the restart may not initiate a restart process until certain conditions are present. For example, activation of the restart (e.g., pressing the button(s) 516, 517) may not initiate the restart process when the surgical robotic system is not in an interrupted state (e.g., when the surgical robotic system is operating normally, or when the surgical robotic system is powered off).

In some embodiments, activation of the restart can restart the entire surgical robotic system, e.g., including the master console 510, one or more slave consoles, and/or an endoscopic device. In other words, the restart of the entire surgical robotic system can be activated using one centralized command. Alternatively, or additionally, one or more components of the surgical robotic system can be selectively restarted, e.g., based on actuation of different combinations or sequences of one or more restart elements. For example, pressing on a button 517 located at or near master manipulator 512a may activate a restart of a left slave console, while pressing on a button 516a or 516b located at or near master manipulator 512b may activate a restart of a right slave console. Such selectively may be useful in instances where a first slave console may have been temporarily interrupted while a second slave console has not been temporarily interrupted.

Figure 10:
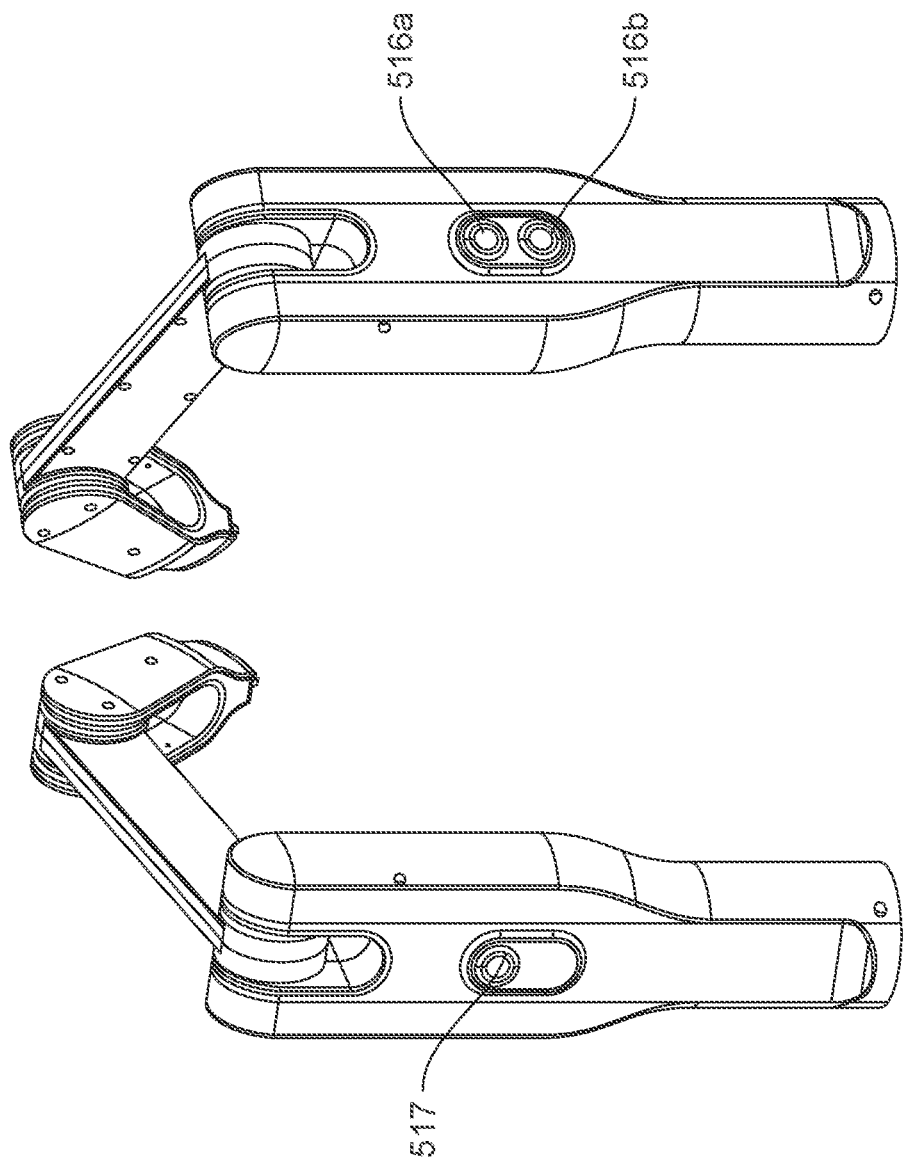
FIG. 10 depicts an example restart of a surgical robotic system, according to embodiments.

While the restart is shown as being located on the master console 510 in the example embodiment depicted in FIGS. 9 and 10, it can be appreciated that the restart can be located at any other location within a sterile zone of the surgical robotic system (e.g., any one of sterile zones 211a, 211b, 215, 221a, 221b, 231 depicted in FIG. 4).

Figure 11:
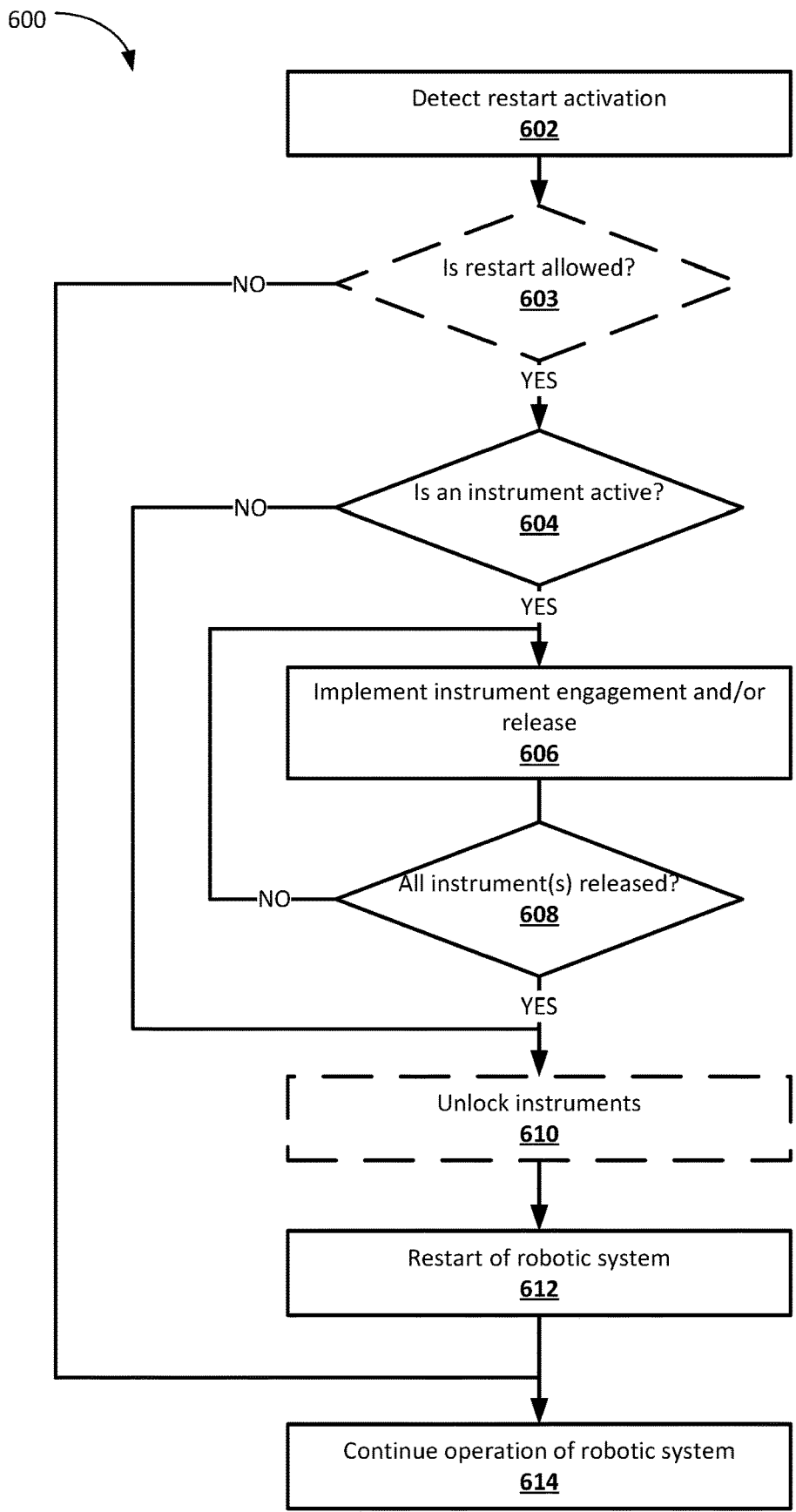
FIGS. 11 and 12 are flow charts of an example method for restarting a surgical robotic system with an instrument release, according to embodiments.
Figure 12:
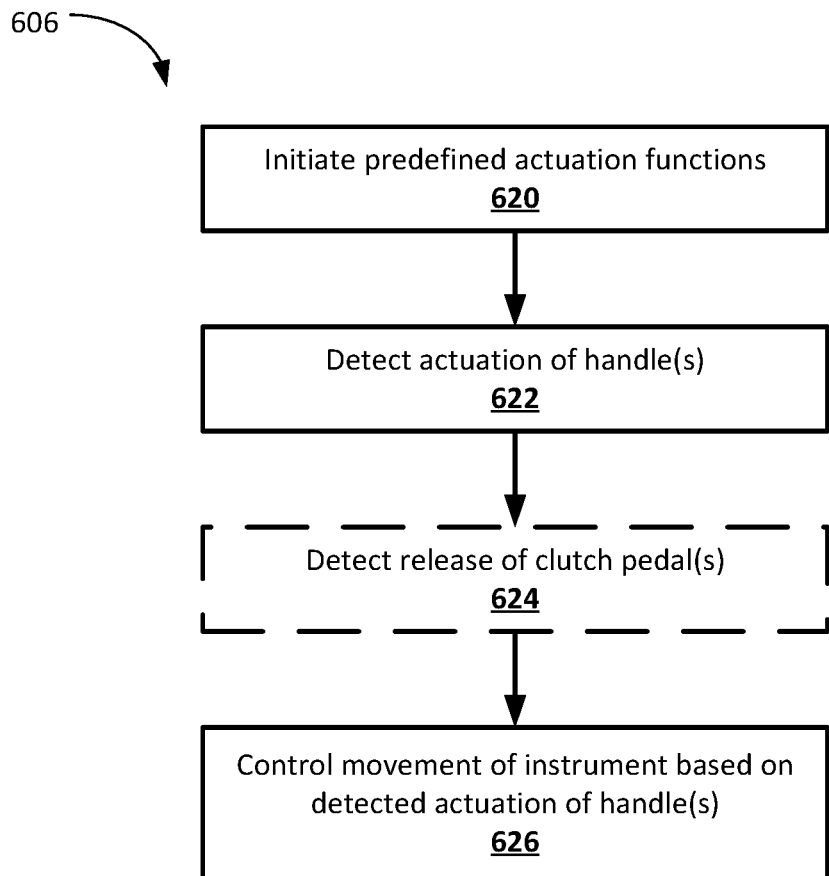
Figure 13:
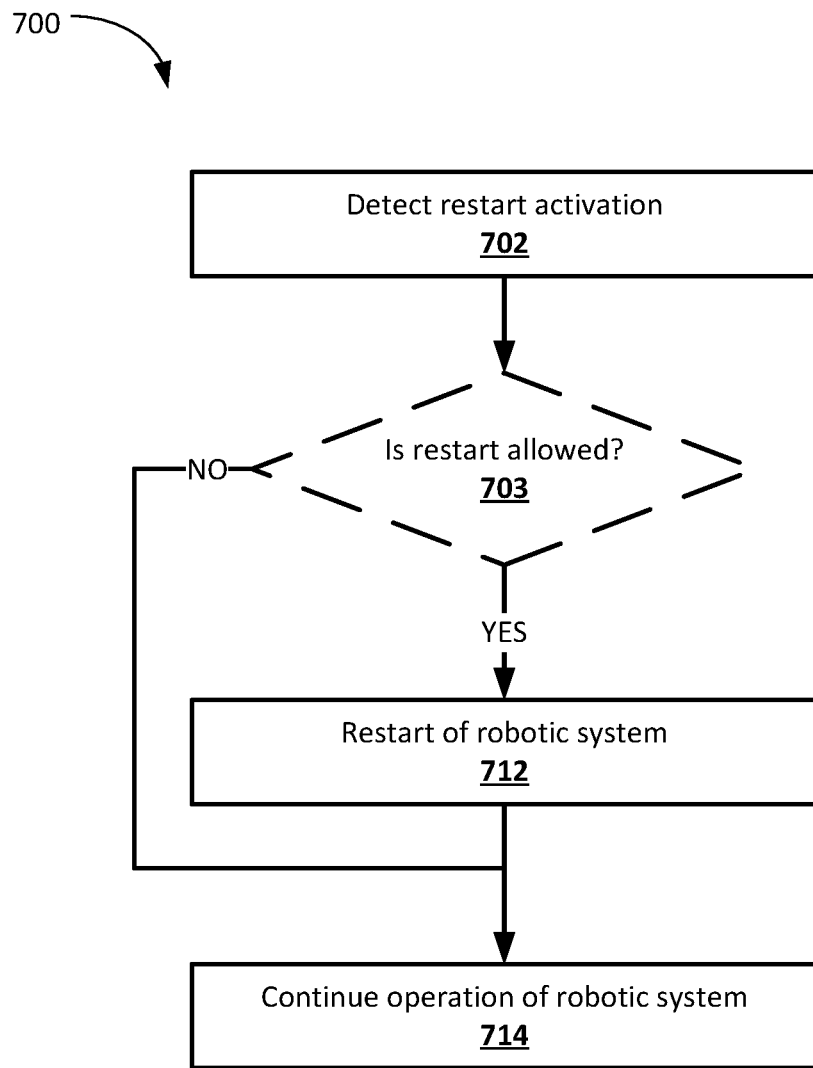
FIG. 13 is a flow chart of an example method for restarting a surgical robotic system, according to embodiments.

FIGS. 11-13 depict various methods of restarting a surgical robotic system while maintaining sterility, according to embodiments. FIGS. 11 and 12 depict a method 600 involving a restart procedure and an instrument release procedure. FIG. 13 depicts a method 700 involving only a restart procedure. The methods 600 and 700 can be implemented by any of the surgical robotic systems described herein, including, for example, surgical robotic system 100, 200, etc. In particular, the methods 600 and 700 can be implemented by one or more processors and/or controllers (e.g., master controller(s) 114, slave controller(s) 124, etc.) of the surgical robotic system.

In some embodiments, a surgeon or other operator within the operating room may control which procedure is implemented by the surgical robotic system. When the surgical robotic system is unexpectedly or temporarily interrupted, the surgical robotic system can be in one of three states of operation. In a first state, the surgical robotic system may not have any instruments present (i.e., no instruments are coupled to the slave manipulators of the surgical robotic system). In such instances, the user can activate a restart, and the surgical robotic system can proceed with restarting according to method 700. In a second state, the surgical robotic system may have one or more instruments present (i.e., one or more instruments are coupled to one or more slave manipulators of the surgical robotic system), but the one or more instruments may not be active or blocked within a patient. In such cases, the instruments do not need to be released and therefore the user may choose to remove the instruments before activating the restart. If the restart is activated without any instruments, then the surgical robotic system can proceed with restarting according to method 700. If there are still instruments present, then the surgical robotic system can proceed with restarting according to method 600. In a third state, the surgical robotic system may have one or more instruments present, and at least one of those instruments may be active or blocked within a patient. In such cases, the user can remove any inactive instruments first and then activate the restart. When the restart is activated, then surgical robotic system can proceed with restarting according to method 600 to release the one or more active instruments.

Referring now to FIG. 11, at 602, the surgical robotic system may detect that a restart has been activated. For example, the surgical robotic system may detect that a user has pressed a restart button or other type of physical actuator. Alternatively, or additionally, the surgical robotic system may detect that a user has actuated or activated a virtual element, such as, for example, a button, slider, switch. Still alternatively, or additionally, the surgical robotic system may detect that a user has spoken a specific command (e.g., as captured by an audio device), made a specific gesture (e.g., as captured by an image capture device), and/or made some other type of indication associated with activating the restart.

At 603, the surgical robotic system may optionally, in response to detecting that the restart has been activated, determine whether restarting is allowed. For example, the surgical robotic system may determine whether certain conditions are present that necessitate a restart. In some embodiments, a restart may only be allowed when one or more components of the surgical robotic system have experienced a temporary interruption. A temporary interruption can be caused by one or more abnormal events or conditions, including, for example, (1) an unexpected movement of a slave manipulator (e.g., a joint or link of a slave manipulator), (2) an unexpected movement of the master console (e.g., the master manipulator or another portion of the master console), (3) an input anomaly associated with the master console (e.g., too fast of a movement of the master manipulator, too high acceleration of the master manipulator, lost of integrity, sensor failure), (4) a collision between a portion of the surgical robotic system (e.g., one or more links of the slave manipulator and/or the instrument) and an external object, or (5) a failure of a sensor, actuator, or controller of the surgical robotic system. When the surgical robotic system is interrupted, it may enter into a safe mode, whereby controlled movement of the slave manipulators by the master console (i.e., telemanipulation of the slave manipulators) may be deactivated. Therefore, in some embodiments, the surgical robotic system may determine whether it is operating in a safe mode, at 603. If the surgical robotic system determines that at least a portion of the surgical robotic system has been temporarily interrupted (e.g., is operating in a safe mode), then the method 600 continues to 604. Alternatively, if the surgical robotic system determines that it is operating normally or has not been interrupted, then the surgical robotic system may continue its normal operation, at 614.

At 604, the surgical robotic system may determine whether an instrument is active. In some embodiments, the surgical robotic system may determine whether an instrument is active by determining whether an instrument is coupled to any one of the slave manipulators of the surgical robotic system. For example, when an instrument is coupled to one of the slave manipulators, then the surgical robotic system may assume that the instrument is active and can proceed to implementing an instrument release procedure, at 606. Alternatively, if no instrument is coupled to a slave manipulator, then the surgical robotic system can proceed to restarting the surgical robotic system, at 612. In some embodiments, the surgical robotic system may determine whether an instrument is active by determining whether an instrument is disposed within a patient. For example, the surgical robotic system may use one or more sensors to determine that an instrument is located within a patient. When an instrument is disposed within a patient, the surgical robotic system may then proceed to implementing an instrument release procedure, at 606. When no instrument is disposed within the patient, then the surgical robotic system may proceed, optionally, to unlocking the instruments, at 610, or to restarting the surgical robotic system, at 612.

At 606, when there is at least one active instrument, the surgical robotic system can implement an instrument release. The surgical robotic system can implement an instrument release by allowing for controlled movement by the master console or telemanipulation of the instrument in a limited or reduced set of DOFs. In embodiments where the instrument includes a set of jaws, the surgical robotic system may enable controlled movement of the instrument in one or two DOFs, including, for example, a first DOF that allows a first jaw to move (e.g., pivot or translate) relative to a second jaw and/or a second DOF that allows the second jaw to move relative to the first jaw. In embodiments where the instrument includes a hook, a scalpel, a spatula, a needle holder, a dissector, a scissor, or a grasper, the surgical robotic system may enable controlled movement of the instrument in one or two DOFs that allows the hook, scalpel, spatula, needle holder, dissector, scissor, or grasper to engage in translational and/or rotational movement. Further details of an example instrument release procedure are described below with reference to FIG. 12.

In some embodiments, the surgical robotic system can implement further engagement of an instrument with patient tissue or other components within a patient. For example, the surgical robotic system may allow for controlled movement by the master console or telemanipulation of the instrument in a limited or reduced set of DOFs that allows the instrument to increase its engagement with patient tissue and/or other components. This can be desirable when a patient is bleeding or when other emergency action may need to be taken within a patient before an instrument is to be released. For example, the instrument can be engaged further with patient tissue to apply pressure to stop bleeding.

Where there are multiple instruments that are coupled to the surgical robotic system (e.g., coupled to one or more slave manipulators of the surgical robotic system), the surgical robotic system may enable instrument release and/or further engagement of the multiple instruments concurrently and/or sequentially. When all instruments have been released, at 608, the method 600 can continue, optionally, to 610 or continue to 612.

In some embodiments, the one or more instruments coupled to the surgical robotic system may be locked in engagement with the slave manipulators, e.g., by one or more locking mechanism(s). In such embodiments, the one or more instruments may need to be released (e.g., the locking mechanism(s) may need to be released) so that the instruments can be removed from the slave manipulators. In some embodiments, the surgical robotic system may optionally unlock the instruments, at 610, such that a sterile user can remove the instruments from the slave manipulators. Alternatively, or additionally, the instruments can be manually unlocked by a user and removed from the slave manipulators.

At 612, the surgical robotic system can automatically restart. In some embodiments, restarting the surgical robotic system can include powering off and on (i.e., power cycling) each component of the surgical robotic system. For example, the master console, each of the slave consoles, and/or the endoscopic device can be powered off and then back on. Optionally, in some embodiments, after powering off and on the surgical robotic system, one or more components of the surgical robotic system may be placed back in a starting or home position. For example, one or more slave manipulators of the surgical robotic system may be placed back in a home position.

At 614, the surgical robotic system may then continue its operation. For example, one or more instruments may be inserted back into the slave manipulators and then the surgical procedure can resume.

FIG. 12 provides a more detailed view of implementing 606 of method 600, according to embodiments. At 620, the surgical robotic system can initiate one or more predefined actuation functions associated with one or more instruments. For example, the surgical robotic system can activate controlled movement by the master console of an instrument in a limited or reduced set of DOFs, as described above. After activating the controlled movement, the surgical robotic system may detect an actuation of one or more handle(s) at the master console, at 622. Optionally, the surgical robotic system may also detect that one or more pedals or other mechanisms for engaging the clutch has been released, at 624. The surgical robotic system may then control the movement of the instrument based on the detected actuation of the handle(s), at 626.

In some embodiments, the surgical robotic system may prevent the user from applying an unintended force on grabbed tissue when taking control of the instrument actuation. In such embodiments, the user may need to first close a handle at the master console and then open the handle until the handle position (or command associated therewith) matches or corresponds to the current position of the instrument (i.e., the position of the instrument when it was interrupted). In response to the handle position matching the current position of the instrument, the actuation of the instrument may then activate and the movement of the handle can be replicated at the instrument. Therefore, in such embodiments, only an opening movement can be the first movement that is replicated. Subsequent movements following the opening of the instrument can then include closing of the instrument (e.g., under visual guidance). Alternatively, in some embodiments (e.g., such as those involving dissention or anastomosis where a vessel may be held open with one or more jaws), the surgical robotic system may require the first movement to be a closing movement.

FIG. 13 depicts method 700 for implementing a sterile restart of the surgical robotic without an instrument release, according to embodiments. At 702, the surgical robotic system may detect that a restart has been activated, similar to 602 of method 600. Optionally, at 703, the surgical robotic system may determine whether restarting is allowed, similar to 603 of method 600. When restarting is allowed, the surgical robotic system may proceed with restarting, at 712, similar to 612 of method 600. When restarting is not allowed, the surgical robotic system may continue its normal operation, at 714, similar to 614 of method 600.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within +10% of the recited value. For example, in some instances, "about 100 [units]" may mean within +10% of 100 (e.g., from 90 to 110). The terms "about" and "approximately" may be used interchangeably.

The indefinite articles "a" and "an." as used herein in the specification and in the claims, unless clearly indicated to the contrary, should be understood to mean "at least one."

The invention claimed is:

1. An apparatus, comprising:
   a restart of a surgical robotic system, the restart including an actuator that is configured to be physically activated by a sterile user from within a sterile filed without compromising the sterile field,
   a controller operatively coupled to the restart, the controller being configured to:
      deactivate, in response to detecting an abnormal event, teleoperation of a slave manipulator of the surgical robotic system or an instrument coupled to the slave manipulator by a user-operated device at a master console of the surgical robotic system; and
      detect that the actuator has been physically activated; and
      after detecting that the actuator has been physically activated, restart the surgical robotic system.

2. The apparatus of claim 1, wherein the actuator includes one or more buttons, switches, or sliders.

3. The apparatus of claim 2, wherein the controller is configured to detect that the actuator has been physically activated when the one or more buttons, switches, or sliders have been physically manipulated for a predefined period of time.

4. The apparatus of claim 2, wherein the controller is configured to detect that the actuator has been physically activated when the one or more buttons, switches, or sliders have been physically manipulated according to a predefined sequence.

5. The apparatus of claim 1, wherein the controller is further configured to provide haptic, audible, or visual feedback while or after the actuator has been physically activated.

6. The apparatus of claim 1, further comprising the master console,
   wherein the user-operated device of the master console includes a first plurality of links that are operatively coupled to a second plurality of links of the slave manipulator such that movements of the first plurality of links cause corresponding movements of the second plurality of links.

7. The apparatus of claim 6, wherein the actuator is located on the master console proximate to the plurality of links.

8. The apparatus of claim 1, wherein the controller is further configured to:

determine whether an instrument is coupled to the slave manipulator; and in response to determining that an instrument is coupled to slave manipulator, enable teleoperation of the instrument in a predefined set of degrees-of-freedom (DOFs) that allows the instrument to engage further with or disengage from tissue or other components within a body of a patient without compromising the sterile field, wherein the controller is configured to restart the surgical robotic system after the instrument has been disengaged from the tissue or other components.

9. The apparatus of claim 8, wherein the instrument includes a set of jaws, and the predefined set of DOFs that allows the instrument to be engaged further with or disengaged from the tissue or other components is one or more DOFs that allow the set of jaws to open or close.

10. The apparatus of claim 8, wherein the instrument includes a hook, scalpel, spatula, needle holder, dissector, scissors, or grasper, and the predefined set of DOFs that allows the instrument to be engaged further with or disengaged from the tissue or other components is a DOF associated with a rotational motion of the hook, scalpel, spatula, needle holder, dissector, scissors, or grasper.

11. The apparatus of claim 1, wherein the controller is further configured to return the slave manipulator to a home position after restarting the robotic system.

12. The apparatus of claim 1, wherein the abnormal event includes at least one of: unexpected movement of at least one of the slave manipulator or the instrument, an input anomaly associated with the master console, a collision between (1) at least one of the slave manipulator or the instrument and (2) an external object, or a failure of a sensor, actuator, or controller of the surgical robotic system.

13. An apparatus, comprising:
a restart of a surgical robotic system that is disposed on a master console of the surgical robotic system at a location behind a sterile barrier that isolates the master console from a sterile field, the restart being configured to be activated by a sterile user from within the sterile field without breaching the sterile barrier;
a controller operatively coupled to the restart, the controller being configured to:
deactivate, in response to detecting an abnormal event, teleoperation of a slave manipulator of the surgical robotic system or an instrument coupled to the slave manipulator by a user-operated device at the master console; and
detect that an actuator has been physically activated; and
after detecting that the actuator has been physically activated, restart the surgical robotic system.

14. The apparatus of claim 13, wherein the restart includes one or more physical or virtual buttons, switches, or sliders.

15. The apparatus of claim 14, wherein the controller is configured to detect that the restart has been activated when the one or more physical or virtual buttons, switches, or sliders have been activated for a predefined period of time.

16. The apparatus of claim 14, wherein the controller is configured to detect that the restart has been activated when the one or more physical or virtual buttons, switches, or sliders have been activated according to a predefined sequence.

17. The apparatus of claim 13, further comprising the master console,
wherein the user-operated device of the master console includes a first plurality of links that are operatively coupled to a second plurality of links of the slave manipulator such that movements of the first plurality of links cause corresponding movements of the second plurality of links.

18. The apparatus of claim 17, wherein the restart is located on the master console proximate to the first plurality of links.

19. The apparatus of claim 13, wherein the controller is further configured to:
determine whether an instrument is coupled to the slave manipulator; and
in response to determining that an instrument is coupled to slave manipulator, enable teleoperation of the instrument in a predefined set of degrees-of-freedom (DOFs) that allows the instrument to engage further with or disengage from tissue or other components within a body of a patient without compromising the sterile field,
wherein the controller is configured to restart the surgical robotic system after the instrument has been disengaged from the tissue or other components.

20. The apparatus of claim 19, wherein the instrument includes a set of jaws, and the predefined set of DOFs that allows the instrument to be engaged further with or disengaged from the tissue or other components is one or more DOFs that allow the set of jaws to open or close.

21. The apparatus of claim 19, wherein the instrument includes a hook, scalpel, spatula, needle holder, dissector, scissors, or grasper, and the predefined set of DOFs that allows the instrument to be engaged further with or disengaged from the tissue or other components is a DOF associated with a rotational motion of the hook, scalpel, spatula, needle holder, dissector, scissors, or grasper.

22. The apparatus of claim 13, wherein the controller is further configured to return the slave manipulator to a home position after restarting the robotic system.

23. The apparatus of claim 13, wherein the abnormal event includes at least one of: unexpected movement of at least one of the slave manipulator or the instrument, an input anomaly associated with the master console, a collision between (1) at least one of the slave manipulator or the instrument and (2) an external object, or a failure of a sensor, actuator, or controller of the surgical robotic system.

* * * * *